US012605350B2

(12) United States Patent
Kim et al.

(10) Patent No.: US 12,605,350 B2
(45) Date of Patent: *Apr. 21, 2026

(54) COMPOSITION FOR PREVENTING, AMELIORATING, OR TREATING DISEASE CAUSED BY NITRATION OF TYROSINE IN PROTEINS COMPRISING TYROSINE AS EFFECTIVE COMPONENT

(71) Applicant: INDUSTRY-ACADEMIC COOPERATION FOUNDATION GYEONGSANG NATIONAL UNIVERSITY, Gyeongsangnam-do (KR)

(72) Inventors: Hyun Joon Kim, Gyeongsangnam-do (KR); Jae Soon Kang, Gyeongsangnam-do (KR); Ji Hyung Baek, Gyeongsangnam-do (KR); Soonwoong Jung, Gyeongsangnam-do (KR); Sang Won Park, Gyeongsangnam-do (KR)

(73) Assignee: INDUSTRY-ACADEMIC COOPERATION FOUNDATION GYEONGSANG NATIONAL UNIVERSITY, Gyeongsangnam-do (KR)

( * ) Notice: Subject to any disclaimer, the term of this patent is extended or adjusted under 35 U.S.C. 154(b) by 585 days.

This patent is subject to a terminal disclaimer.

(21) Appl. No.: 18/013,412

(22) PCT Filed: Jun. 30, 2021

(86) PCT No.: PCT/KR2021/008259
§ 371 (c)(1),
(2) Date: Dec. 28, 2022

(87) PCT Pub. No.: WO2022/005201
PCT Pub. Date: Jan. 6, 2022

(65) Prior Publication Data
US 2023/0248681 A1      Aug. 10, 2023

(30) Foreign Application Priority Data

Jun. 30, 2020    (KR) ........................ 10-2020-0080308

(51) Int. Cl.
| | |
|---|---|
| A61K 31/198 | (2006.01) |
| A23L 33/175 | (2016.01) |
| A61P 1/16 | (2006.01) |
| A61P 3/00 | (2006.01) |
| A61P 13/12 | (2006.01) |
| A61P 25/00 | (2006.01) |

(52) U.S. Cl.
CPC .......... A61K 31/198 (2013.01); A23L 33/175 (2016.08); A61P 1/16 (2018.01); A61P 3/00 (2018.01); A61P 13/12 (2018.01); A61P 25/00 (2018.01)

(58) Field of Classification Search
CPC .................................................... A61K 31/198
See application file for complete search history.

(56) References Cited

U.S. PATENT DOCUMENTS

| | | | |
|---|---|---|---|
| 9,447,157 B2 | 9/2016 | Black et al. | |
| 2004/0204452 A1 | 10/2004 | Blume et al. | |
| 2011/0033868 A1 | 2/2011 | Bottari et al. | |
| 2024/0050513 A1* | 2/2024 | Kim ........................ | A23L 33/17 |

FOREIGN PATENT DOCUMENTS

| | | |
|---|---|---|
| CN | 1070827 A | 4/1993 |
| CN | 101084925 A | 12/2007 |
| CN | 101332209 A | 12/2008 |
| CN | 101332210 A | 12/2008 |
| CN | 102818896 A | 12/2012 |
| CN | 103209697 A | 7/2013 |
| CN | 103998033 A | 8/2014 |
| CN | 110922469 A | 3/2020 |
| KR | 10-1048657 B1 | 7/2011 |
| KR | 10-2020-0049359 A | 5/2020 |

(Continued)

OTHER PUBLICATIONS

European Search Report For EP21832930.8 issued on Jun. 5, 2024 from European patent office in a counterpart European patent application.
Office action issued on Sep. 27, 2024 from China Patent Office in a counterpart China Patent Application No. 202180047217.6 (all the cited references are listed in this IDS.) (English translation is also submitted herewith.).
Office action issued on Sep. 9, 2024 from Japan Patent Office in a counterpart Japan Patent Application No. 2022-581606 (all the cited references are listed in this IDS.) (English translation is also submitted herewith.).

(Continued)

*Primary Examiner* — John S Kenyon
(74) *Attorney, Agent, or Firm* — The PL Law Group, PLLC

(57) ABSTRACT

A method for ameliorating a disease caused by nitration of tyrosine in protein includes administering a composition comprising tyrosine or a salt thereof to a subject in need thereof. Tyrosine as effective component of the present invention not only can enhance the activity of glutamine synthetase having reduced activity and but also has an effect of restoring the amount (i.e., ratio) of glutamine and glutamic acid in brain and the amount of ammonia to normal level, an effect of enhancing the insulin sensitivity in a model of type 2 diabetes, an effect of suppressing the excitotoxicity and oxidative stress in a model of epileptic seizure, an effect of reducing cerebral infarction and enhancing the activity of GS in a model of brain stroke, an effect of eliminating the nitration of tyrosine using human recombinant MnSOD, and an effect for acute renal failure and hyperammonemia.

7 Claims, 22 Drawing Sheets

Specification includes a Sequence Listing.

(56) References Cited

FOREIGN PATENT DOCUMENTS

| | | |
|---|---|---|
| WO | WO 2012/020991 A2 | 2/2012 |
| WO | WO 2018/079832 A1 | 5/2018 |
| WO | WO 2018/215780 A1 | 11/2018 |
| WO | WO 2019/018633 A1 | 1/2019 |

OTHER PUBLICATIONS

Cui Jianhua et al., "Effect of Folium Ginkgo on Plasma Level of Ammo and Lactic Acid of Human After Exercise at High Altitude", Journal of Plateau Medicine, vol. 15(3), 2005 (English translation of abstract in the third page is submitted herewith.).

L-Tyrosine 100g, Supplement, Food Additivies, Food, Margo web site: <URL: https://web.archive.org/web/20170308050731/https://marugo.org/products/detail62.html> (English translation of contents is submitted herewith.).

International Search Report for PCT/KR2021/008259 mailed on Oct. 7, 2021.

Kayacan Yildirim et al., "The effects of moderate running exercise and L-tyrosine on penicillin-induced epileptiform activity in rats", Acta Neurobiologiae Experimentalis, vol. 79, pp. 148-154, 2019 (http://dx.doi.org/10.21307/ane-2019-013).

Yamori Yukio, "Prophylactic trials for stroke in stroke-prone SHR (SHRSP) (5) Mechanism of blood pressure reduction by tyrosine administration", Japanese Heart Journal, vol. 21, Nr:4, p. 576, 1980.

Young Simon N, "L-Tyrosine to alleviate the effects of stress?", Journal of Psychiatry & Neuroscience, vol. 32, Nr:3, p. 224, 2007.

Gelenberg Alan J, "Tyrosine for the treatment of depression", Am J Psychiatry, vol. 137, No. 5, pp. 622-623, 1980.

Office action issued on Jan. 27, 2024 from China Patent Office in a counterpart China Patent Application No. 202180047217.6 (all the cited references are listed in this IDS.) (English translation is also submitted herewith.).

Office action issued on Mar. 4, 2024 from Japan Intellectual Property Office in a counterpart Japanese Patent Application No. 2022-581606 (all the cited references are listed in this IDS.) (English translation is also submitted herewith.).

Alan J. Gelenberg, M.D. et al., "Tyrosine for the Treatment of Depression", Nutrition and Health, 1984, vol. 3, pp. 163-173, DOI: 10.1177/026010618400300305.

Tyrosine : Activation of brain cells, Dec. 29, 2019, Search date : Feb. 9, 2024, (WEB archive use) (English machine translation is submitted herewith.).

Domestic L-Tyrosine Supplement Power of Awakening Premium 1 tablet 250mg Daily intake 750mg 1 month 22500mg Tyrosine combination supplement 90 tablets 1 month supply Vitamin B6 and folic acid combination (Amazon Online use) (English machine translation is submitted herewith).

Keiki Ogino, "3-NitroTyrosine", Okayama University Graduate School of Medicine, Dentistry and Pharmaceutical Sciences Sanitary Science, Okayama Igakkai Magazine , Jan. 2007, 118th Volume, pp. 225-234 (English translation of Abstract is submitted herewith).

Takashi Matsumoto, et al., "The ability of the various biological substances to delete peroxynitrite light", Gakuen life environment studies, Dec. 2008, No. 818, pp. 35-39. (English Abstract is included in the first page.).

Frears E. R., "Inactivation of tissue inhibitor of metalloproteinase-1 by peroxynitrite", FEBS Letters., 1996, vol. 381, pp. 21-24, DOI. 10.1016/0014-5793(96)00065-8.

Tayyeba K. Ali et al., "Peroxynitrite Mediates Retinal Neurodegeneration by Inhibiting Nerve Growth Factor Survival Signaling in Experimentaland Human Diabetes", Diabetes, 2008, vol. 57, No. 4, pp. 889-898, DOI.10.2337/db07-1669.

Yamori, Yukio, "Prophylactic Trials for Stroke in Stroke-prone SHR (SHRSP) (5) Mechanism of Blood Pressure Reduction by Tyrosine Administration", Japanese Heart Journal, vol. 21, No. 4, p. 576, 1980 ; published on J-Stage ( https://www.jstage.jst.go.jp/article/ihj1960/21/4/21_4_576/_pdf/-char/en) Dec. 9, 2008 (Sep. 12, 2008).

* cited by examiner (A)

COMPOSITION FOR PREVENTING, AMELIORATING, OR TREATING DISEASE CAUSED BY NITRATION OF TYROSINE IN PROTEINS COMPRISING TYROSINE AS EFFECTIVE COMPONENT

CROSS REFERENCE TO RELATED APPLICATIONS AND CLAIM OF PRIORITY

This application claims benefit under 35 U.S.C. 119, 120, 121, or 365(c), and is a National Stage entry from International Application No. PCT/KR2021/008259 filed on Jun. 30, 2021, which claims priority to the benefit of Korean Patent Application No. 10-2020-0080308 filed in the Korean Intellectual Property Office on Jun. 30, 2020, the entire contents of which are incorporated herein by reference.

BACKGROUND

1. Technical Field

The present invention relates to a composition for preventing, ameliorating, or treating a disease caused by nitration of tyrosine in proteins comprising tyrosine as effective component.

2. Background Art

If •NO or •NO-derived metabolites are present in human body, excessive amount of the reactive oxygen species causes generation of nitrate species such as nitrogen peroxide. Thus, when nitration of tyrosine occurs among the amino acids included in proteins, a structural and functional change of the proteins may be caused. Accordingly, nitration of tyrosine may become the reason of having various diseases.

For example, as an enzyme for synthesizing glutamine in human body by using glutamic acid and ammonia, glutamine synthetase (GS) is produced in many organs of the human body and it plays a role in nitrogen balance in the human organs and body. When glutamine synthetase is exposed to active nitrogen due to chronic stress or the like, tyrosine is nitrated, which results in less active glutamine synthetase to cause various diseases.

In recent years, gene therapy based on overexpression of glutamine synthetase in skeletal muscles has been suggested for treating acute hyperammonemia. Basic principle of the gene therapy involves replacing or enhancing glutamine synthetase, which is generally deficient in the muscles of a patient suffering from liver disease, so that ammonia removal by glutamine synthetase can be promoted in the muscles.

Meanwhile, in Korean Patent Application Publication No. 2020-0018488, use of glutamine synthetase for treating hyperammonemia is disclosed, and, in Korean Patent Application Publication No. 2020-0038481, a composition for treating stress-related disorder is disclosed. However, so far there is no disclosure of a composition for preventing, ameliorating, or treating a disease caused by nitration of tyrosine in proteins comprising tyrosine as effective component as it is described in the present invention.

SUMMARY

The present invention is devised under the circumstances that are described in the above and provided in the present invention is a composition for preventing, ameliorating, or treating a disease caused by nitration of tyrosine in proteins comprising tyrosine as effective component. It was found that tyrosine as effective component of the present invention not only can reduce the amount of N-Tyr in glutamine synthetase, which is produced due to stress, but also has an effect of enhancing the activity of glutamine synthetase having reduced activity and restoring the amount of glutamine and glutamic acid in brain and the amount of ammonia to normal level. In addition, by finding the effect of enhancing the insulin sensitivity in a model of type 2 diabetes, effect of suppressing the excitotoxicity and oxidative stress in a model of epileptic seizure, effect of reducing cerebral infarction and enhancing the activity of GS in a model of brain stroke, effect of eliminating the nitration of tyrosine using human recombinant MnSOD, and effect for acute renal failure and hyperammonemia, the present invention is completed accordingly.

To achieve the object described in the above, the present invention provides a functional health food composition for preventing or ameliorating a disease caused by nitration of tyrosine in proteins comprising, as effective component, tyrosine or a salt thereof that is acceptable for use in food product.

The present invention further provides a pharmaceutical composition for preventing or treating a disease caused by nitration of tyrosine in proteins comprising, as effective component, tyrosine or a pharmaceutically acceptable salt thereof.

The present invention still further provides a method of removing a nitro group from nitrated tyrosine by treating a protein containing nitrated tyrosine with tyrosine.

The present invention relates to a composition for preventing, ameliorating, or treating a disease caused by nitration of tyrosine in proteins comprising tyrosine as effective component. It was found that, while the expression amount of glutamine synthetase remains unchanged under stress condition, amount of N-Tyr in GS shows a statistically significant increase, resulting in lower activity of GS. Furthermore, it was found based on cell-based experiments that free tyrosine has an effect of strengthening the low activity of GS, effect of restoring the amount (i.e., ratio) of glutamine and glutamic acid in brain and the amount of ammonia to normal level, effect of enhancing the insulin sensitivity in a model of type 2 diabetes, effect of suppressing the excitotoxicity and oxidative stress in a model of epileptic seizure, effect of reducing cerebral infarction and enhancing the activity of GS in a model of brain stroke, effect of eliminating the nitration of tyrosine using human recombinant MnSOD, and effect for acute renal failure and hyperammonemia.

BRIEF DESCRIPTION OF THE DRAWINGS

FIG. 19 shows the result of determining the denitration effect of tyrosine, in which the determination was made by using human recombinant MnSOD. * indicates that the tyrosine administration group (L-Tyr, D-Tyr) has higher MnSOD activity compared to the nitrogen peroxide (2.1 mM PN) group, in which * has $p<0.001$.

FIG. 20 shows the result of determining the effect of tyrosine on acute renal failure, in which (A) shows the gene expression amount of NQO-1 as an anti-oxidation factor, (B) shows the activity of Cu/ZnSOD, (C) shows the activity of MnSOD, (D) shows the amount of ROS/RNS, and (E) shows the expression amount of nitrotyrosine proteins in kidney tissues 24 hours after renal ischemia and reperfusion.

DETAILED DESCRIPTION

Figure 1:
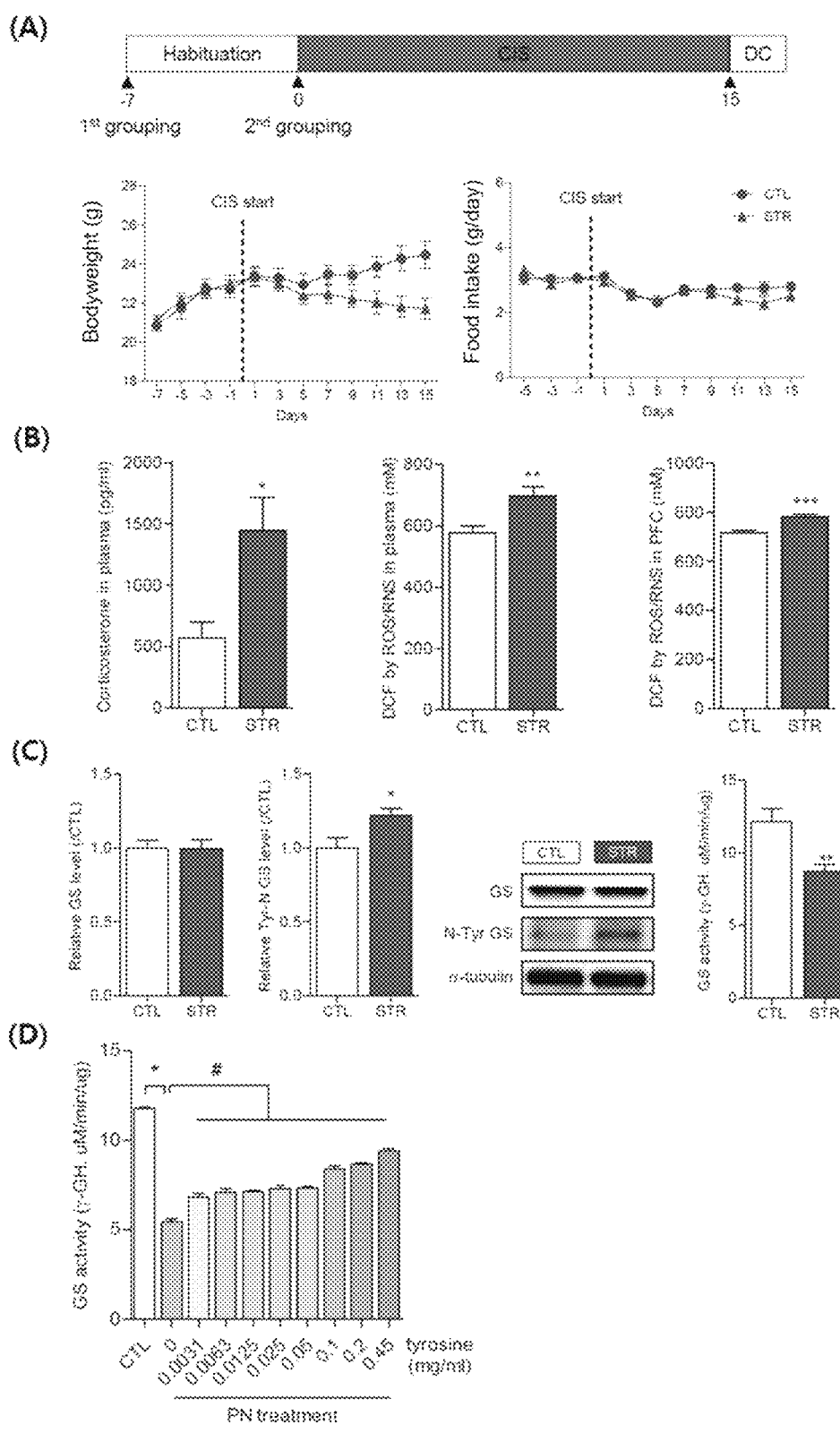
FIG. 1 shows the result of determining the effect against chronic immobilization stress (CIS), including (A) the result of examining a change in bodyweight and food intake during the test period, (B) the result of examining a change in corticosterone amount in plasma and also a change in ROS/RNS amount in plasma and prefrontal cortex (PFC), (C) the result indicating that, although there was no change in GS amount, N-Tyr amount shows a statistically significant increase and GS activity shows a statistically significant decrease in the stress group, and (D) the result of examining the in vitro GS activity after treating PFC tissue lysate with nitrogen peroxide and tyrosine. *, , and * indicate that there is a statistically significant difference compared to CTL, in which * has $p < 0.05$,  has $p < 0.01$, and * has $p<0.001$, and #indicates that there is a statistically significant increase in GS activity in the group treated with tyrosine compared to the group not treated with any tyrosine, in which #has $p<0.05$.

The present invention relates to a functional health food composition for preventing or ameliorating a disease caused by nitration of tyrosine in protein comprising, as effective component, tyrosine or a salt thereof that is acceptable for use in food product.

The aforementioned nitration of tyrosine in protein is preferably nitration of tyrosine in any protein selected from tyrosine hydroxylase, Mn superoxide dismutase, Cu/Zn superoxide dismutase, insulin receptor β subunit, annexin IV, glutamate dehydrogenase, 3-α-OH steroid dehydrogenase, glutathione S-transferase, 3-ketoacyl CoA thiolase, catalase, Tau protein, mitochondria complex 1, α-synuclein, apolipoprotein-A1, amyloid-β, and NMDA receptor, but it is not limited thereto.

The aforementioned disease caused by nitration of tyrosine in protein is preferably anyone selected from depressive disorder, anxiety disorder, stroke, epilepsy, glaucoma, diabetes, diabetic retinopathy, seizure, hepatic encephalopathy, cognitive impairment, brain development impairment, cancer, Alzheimer's disease, acute kidney injury, and hyperammonemia, but it is not limited thereto.

The aforementioned nitration of tyrosine in proteins may occur in brain, liver, muscle, fat tissues, kidney tissues, pancreas, or lung, but it is not limited thereto.

The administration amount of tyrosine as an effective component of the present invention is preferably the amount disclosed in the following Table 1, but it is not limited thereto.

TABLE 1

| Administration amount and diet period for various diseases | | | |
| --- | --- | --- | --- |
| Name of disease | Administration amount of tyrosine (based on mouse) | | Diet period |
| | Animal feed | Diet amount | |
| Depressive disorder, Cognitive impairment | 180 to 1,000 mg/kg of diet | 14 to 140 mg/kg/day | 4 weeks |
| Epilepsy | 180 to 1,000 mg/kg of diet | 14 to 140 mg/kg/day | 1 week |
| Stroke | 800 to 1000 mg/kg of diet | 80 to 140 mg/kg/day | 1 week |

TABLE 1-continued

| Administration amount and diet period for various diseases | | | |
| --- | --- | --- | --- |
| Name of disease | Administration amount of tyrosine (based on mouse) | | Diet period |
| | Animal feed | Diet amount | |
| Diabetes | 180 mg/kg of diet | 14 to 28 mg/kg/day | 15 weeks |
| Acute renal failure | 100 mg/kg of bodyweight | 100 mg/kg | 4 days |
| Hepatic encephalopathy (Hyperammonemia) | 100 mg/kg of bodyweight | 100 mg/kg | 4 days |

The functional health food composition may be produced as anyone selected from a pill, a tablet, a capsule, a powder preparation, powders, a granule, a candy, a syrup, and a drink, or the production may be carried out by adding it as an ingredient of a food product. The functional health food composition can be suitably produced according to a general method.

As an example of the food product to which the effective component of the present invention can be added, it can be in the form that is any one selected from meat, sausage, bread, chocolate, candies, snacks, biscuits, pizza, ramen, other noodles, gums, dairy products including ice cream, various kinds of soup, beverage, tea, drink, alcohol beverage, and vitamin complex, and all functional health food products in general sense are included therein.

The functional health food composition of the present invention may further comprise various nutritional supplements, a vitamin, a mineral (i.e., electrolyte), a synthetic or natural flavor, a coloring agent, an enhancing agent (i.e., cheese, chocolate, or the like), pectinic acid and a salt thereof, alginic acid and a salt thereof, an organic acid, a protective colloidal thickening agent, a pH adjusting agent, a stabilizer, a preservative, glycerin, alcohol, and a carbonating agent used for carbonated drink. Other than those, natural fruit juice or fruit pulp for producing vegetable drink may be additionally comprised. Those ingredients may be used either singly or in combination thereof.

The functional health food composition of the present invention may further comprise various flavoring agents, natural carbohydrates, or the like as an additional component. Examples of the natural carbohydrates include monosaccharides like glucose and fructose, disaccharides like maltose and sucrose, polysaccharides like dextrin and cyclodextrin, and sugar alcohols like xylitol, sorbitol, and erythritol. As a sweetening agent, natural sweetening agent like thaumatin and stevia extract and synthetic sweetening agent like saccharine and aspartame can be used.

The present invention further relates to a pharmaceutical composition for preventing or treating a disease caused by nitration of tyrosine in protein comprising, as effective component, tyrosine or a pharmaceutically acceptable salt thereof.

In addition to the tyrosine described above, a pharmaceutically acceptable carrier, vehicle, or diluent may be additionally comprised. The pharmaceutical composition of the present invention can be administered either orally or parenterally. In case of parenteral administration, it is preferable to choose external application on skin, or intraperitoneal, rectal, intravenous, muscular, or subcutaneous injection, but it is not limited thereto.

The pharmaceutical composition of the present invention may be produced by using a diluent or a vehicle like a filling agent, a bulking agent, a binding agent, a wetting agent, a disintegrating agent, and a surfactant. Examples of the solid preparation for oral administration include a tablet, a pill, a powder preparation, a granule, and a capsule. The solid preparation is produced by mixing at least one compound with one or more vehicles such as starch, calcium carbonate, sucrose, lactose, or gelatin. Furthermore, other than simple vehicles, a lubricating agent such as magnesium stearate or talc is also used. As for the liquid preparation for oral administration, a suspension, a solution preparation for internal use, an emulsion, a syrup preparation, or the like can be mentioned. Other than water or liquid paraffin commonly used as a simple diluent, various kinds of a vehicle such as moisturizing agent, sweetening agent, aromatic agent, or preservatives may be included. Examples of a preparation for parenteral administration include a sterilized aqueous solution, a non-aqueous preparation, a suspension preparation, an emulsion preparation, a freeze-dried preparation, and a suppository preparation. As a non-aqueous preparation or a suspending preparation, propylene glycol, polyethylene glycol, or vegetable oil such as olive oil, and injectable ester such as ethyl oleate can be used. As a base for a suppository preparation, witepsol, macrogol, tween 61, cacao fat, laurin fat, glycerol, gelatin, or the like can be used.

The composition according to the present invention is administered in a pharmaceutically effective amount. As described herein, the expression "pharmaceutically effective amount" means an amount sufficient for treating a disorder at reasonable benefit-risk ratio that can be applied for a medical treatment. The effective dose level may be determined based on a type or severeness of a disorder of a patient, activity of a pharmaceutical, sensitivity to a pharmaceutical, administration period, administration route, excretion ratio, time period for therapy, elements including a pharmaceutical used in combination, and other elements that are well known in the medical field. The composition of the present invention can be administered as a separate therapeutic agent, or it can be used in combination with other therapeutic agents. It can be administered in order or simultaneously with a conventional therapeutic agent. It can be also administered as single-dose or multi-dose. It is important to administer an amount which allows obtainment of the maximum effect with minimum dose while considering all of the aforementioned elements without having any side effect, and the dosage can be easily determined by a person skilled in the pertinent art.

The dosage of the composition of the present invention may vary in a broad range depending on bodyweight, age, sex, health state, diet of a patient, administration period, administration method, excretion rate, and severeness of disorder.

The present invention still further relates to method of removing a nitro group from nitrated tyrosine by treating a protein containing nitrated tyrosine with tyrosine.

Hereinbelow, the present invention is explained in greater detail in view of the Examples. However, the following Examples are given only for more specific explanation of the present invention and it would be evident to a person who has common knowledge in the pertinent art that the scope of the present invention is not limited by them.

EXAMPLES

1. Animal Model

In the present invention, twenty-eight C57BL/6 male mice (7-week old, KOATECH, South Korea) were kept under standard conditions (i.e., temperature of 22 to 24° C., humidity of 50 to 70%, and 12-hour light/dark cycle with lighting on 6 AM), and the animals were allowed to have free access to diets and water. The animals used for the present invention were handled according to the protocol (GNU-161128-M0068) acknowledged by Gyeongsang National University Institutional Animal Care and Use Committee (GNU IACUC), which follows the guidelines of NIH (Bechesda, Md., USA).

2. Preparation of Plasma and Prefrontal Cortex (PFC) Sample

Each of the blood and PFC sample was obtained from a mouse anesthetized with $CO_2$ gas. Specifically, mouse blood was collected between 9 AM and 11 AM and stored in a $K_3$EDTA-coated vacuum container. Plasma was obtained by centrifuge for 10 minutes at 4° C., 500×g. PFC sample was weighed first, and, after lysis of the tissues by using Bullet homogenizer, subjected to centrifuge for 20 minutes at 4° C., 12,000 rpm. Thus-obtained plasma and tissue lysate were kept at −80° C. until use.

3. Determination of the Glutamine Synthetase (GS) Activity and the Levels of Tyr-Nitrated GS 10 μg of the lysate were admixed with 50 ml of GS assay buffer solution (50 mM imidazole-HCl, pH 6.8, 50 mM L-glutamine, 25 mM hydroxylamine, 25 mM sodium arsenate, 2 mM $MnCl_2$ and 0.16 mM ADP), followed by incubation for 1 hour at 37° C.

After the mixing, the reaction was terminated by adding 50 μl of stop buffer solution (90 mM $FeCl_3$, 1.8 N HCl and 1.45% trichloroacetic acid), and then γ-glutamylhydroxamate synthesized from a reaction between glutamine and hydroxylamine as catalyzed by GS was measured at 560 nm using a microplate reader.

By using Western blot (WB) and immunoprecipitation (IP)-WB, level of GS and level of Tyr-nitrated GS were measured, respectively. The immunoprecipitation analysis of Tyr-nitrated GS was carried out using anti-3-nitrotyrosine antibody (ab61392, Abcam, Cambridge, UK) and protein A/G Plus agarose (Santa Cruz, Dallas, TX, USA) by following the manufacturer's protocol. GS Western blot was carried out by using anti-GS (1:5000, Abcam).

Example 1. Behavior Analysis after Chronic Immobilization Stress (CIS) and Measurement of Change in Activity of Glutamine Synthetase (GS) and Amount of Nitrated Tyrosine in GS The animal models were divided into two groups (i.e., normal group and stress group). The animal of stress group was individually brought by force to a restrainer for 2 hours every day (i.e., between 2 PM and 4 PM) so that it was applied with chronic immobilization stress for 15 days. Change in bodyweight and feed intake amount were measured every other day.

After that, the animal was sacrificed, and a change in corticosterone amount in plasma was examined. ROS/RNS in plasma and PFC was also examined. The corticosterone amount was examined using an ELISA kit (Cayman) by following the manufacturer's protocol, and ROS/RNS was also examined using an ROS/RNS assay kit (Cell Biolabs, San Diego, CA, USA) by following the manufacturer's protocol.

As a result, it was found as shown in FIG. 1 that the bodyweight of the stress group applied with chronic stress tends to decrease between Day 7 and Day 15 compared to the control group which has not been applied with any stress (CTL). However, there was almost no difference in terms of the food intake amount, and corticosterone amount and ROS/RNS also showed a statistically significant increase.

Meanwhile, compared to the control group, no decrease in the expression amount of glutamine synthetase (GS) was shown from the stress group. It was further found that the level of nitrated tyrosine in GS exhibits a statistically significant increase and GS activity shows a statistically significant decrease.

Moreover, after PFC (prefrontal cortex) tissue lysate (10 μg) was added and mixed with 0.0031 to 0.45 mg/ml tyrosine, incubated on ice for 10 minutes, and added with nitrogen peroxide (PN), in an amount that is 10 times the tissue lysate, followed by incubation for 10 minutes, in vitro GS activity was examined. As a result, it was found that higher GS activity is obtained in accordance with an increase in the tyrosine concentration.

Example 2. Determination of Change in Bodyweight and Food Intake Amount in Chronic Immobilization Stress Group (STR) Fed with Tyrosine-Diet (TD)

The animal models were divided into two groups (i.e., normal group and stress group). The animal of stress group was individually brought by force to a restrainer for 2 hours every day (i.e., between 2 PM and 4 PM) so that it was applied with chronic immobilization stress for 15 days. Change in bodyweight and food intake amount were measured every other day.

The normal group and stress group were divided again into a normal diet group and a tyrosine-supplemented diet group (181.2 mg/kg), and then fed.

Figure 2:
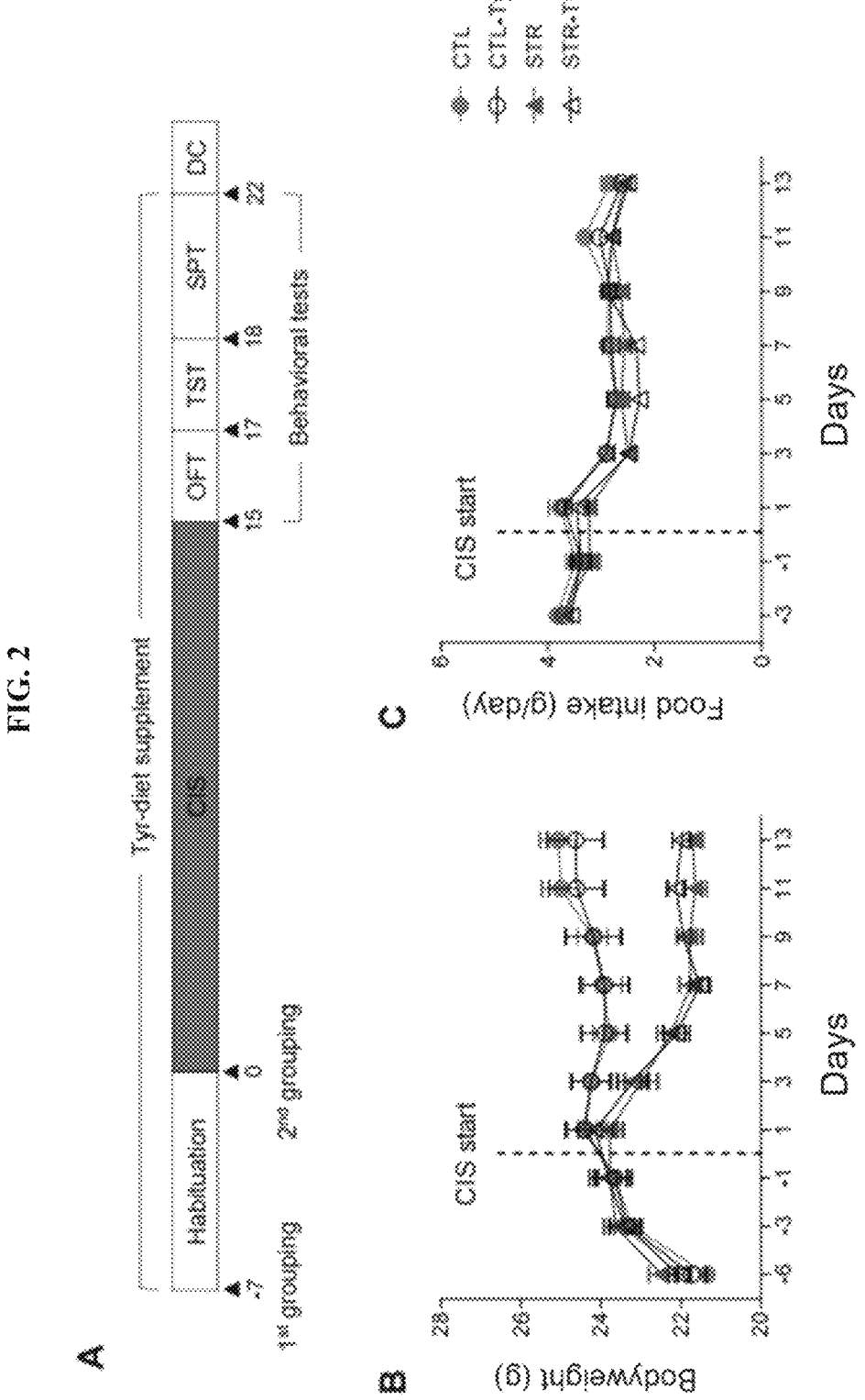
FIG. 2 shows the result of determining the bodyweight and feed intake amount in the chronic immobilization stress group (STR), which has been fed with tyrosine-diet (TD), including (A) the schedule of normal diet group (ND) and tyrosine-diet group (TD), (B) the result of examining a change in bodyweight, and (C) the result of examining the food intake amount.

As a result, it was found as shown in FIG. 2 that there is no change in bodyweight or any difference in food intake amount depending on the presence or absence of tyrosine diet.

After that, behavior analysis including OFT (open field test), TST (tail suspension test), and SPT (sucrose preference test) was carried out.

OFT (open field test) was carried out using a rectangular box (60×60×20 cm). Mouse was placed at the center area of box (30×30 cm), and the mouse movement was followed for 5 minutes and total travel distance, center area duration, and frequency of center area entries were measured.

For TST (tail suspension test), the mouse was individually hung in a box with horizontal bar. To measure the immobile duration, animal movement was followed for 6 minutes.

For SPT (sucrose preference test), 0.1 M sucrose and water were provided for 48 hours so that the animals are habituated with them. After that, none of 0.1 M sucrose and water was provided for 24 hours, and then 0.1 M sucrose and water were provided again for 6 hours. Then, 0.1 M sucrose and water were moved to different positions for 3 hours.

After that, consumption amount of sucrose and water was measured, and the sugar preference was calculated in terms of the ratio of provided sucrose compared to total consumption amount.

Figure 3:
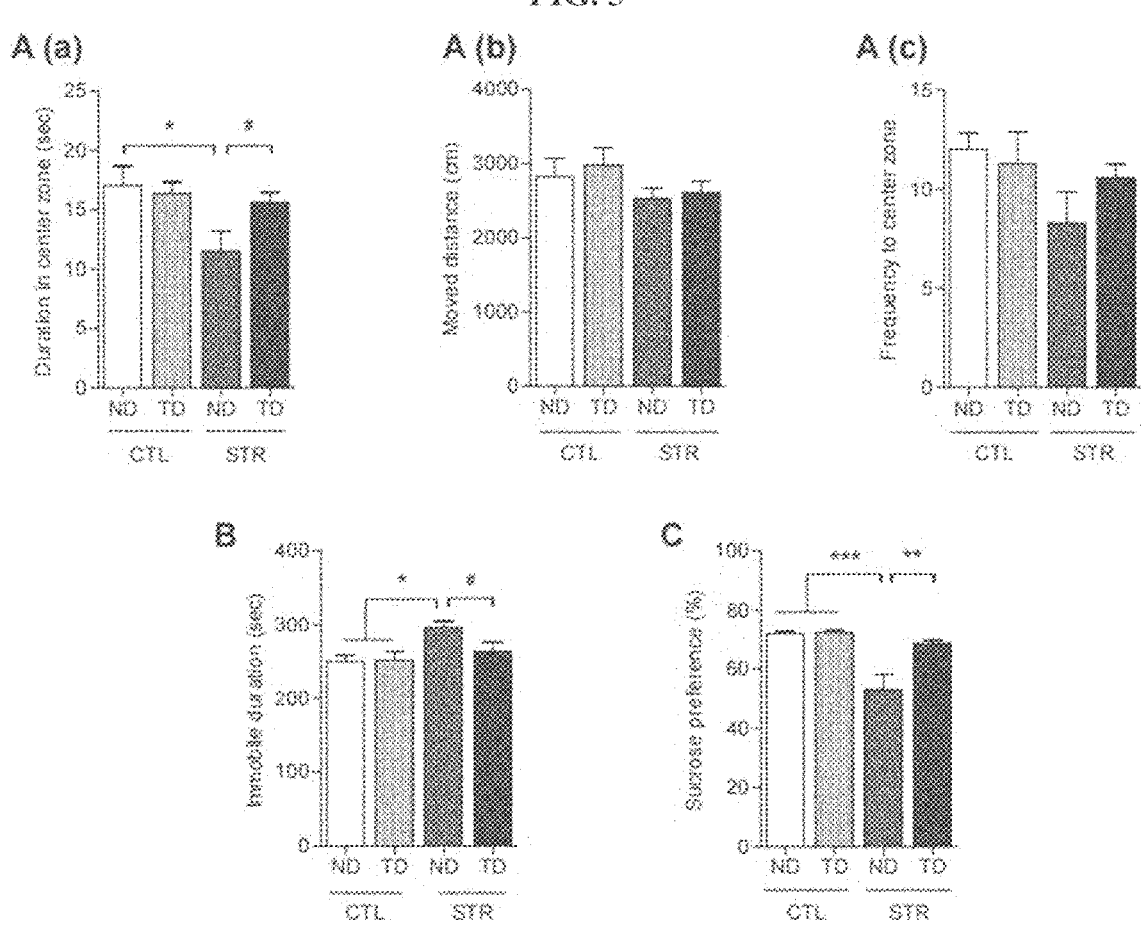
FIG. 3 shows the result of determining the depressive behavior in the chronic immobilization stress group (STR), which has been fed with tyrosine-diet (TD), including (A) the result of open field test, (B), the result of tail suspension test, and (C) the result of sucrose preference test.

As a result, it was found as illustrated in FIG. 3 that, according to the open field test, the center area duration, travel distance, and frequency of center area entries are smaller in the stress group (STR) compared to the normal group (CTL). However, among the stress groups, the tyrosine-diet group (TD) showed higher center area duration, travel distance, and frequency of center area entries compared to the normal diet group (ND).

Moreover, according to the TST (tail suspension test), in the normal diet group (ND) of the stress group, there is a statistically significant increase in immobile duration compared to the normal group (CTL) (p<0.05). On the contrary, the tyrosine-diet group showed a statistically significant decrease in immobile duration (p<0.05).

Moreover, also according to the sugar preference stress, there is a statistically significant decrease the sugar preference in the stress group compared to the normal group (p<0.001). However, there is a statistically significant increase in the sugar preference in the tyrosine diet group of the present invention compared to the normal diet group of the stress group (p<0.01).

Figure 4:
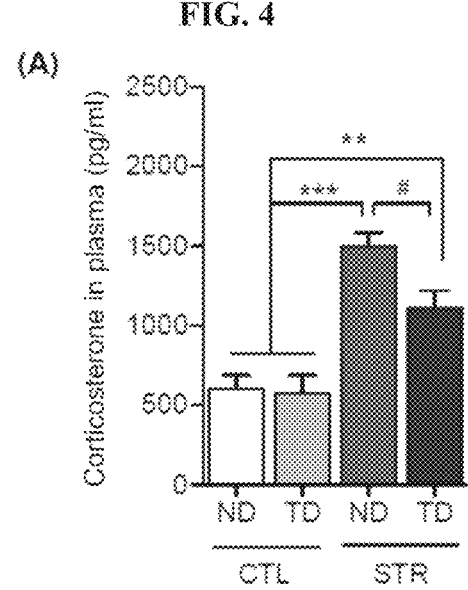
FIG. 4 shows the result of determining (A) corticosterone amount in plasma from the chronic immobilization stress group (STR), which has been fed with tyrosine-diet (TD), and (B) and (C) stress hormone and oxidative stress reduced by TD, in which a change in ROS/RNS in plasma or PFC was followed by using DCF (dichlorofluorescin).
Figure 4:
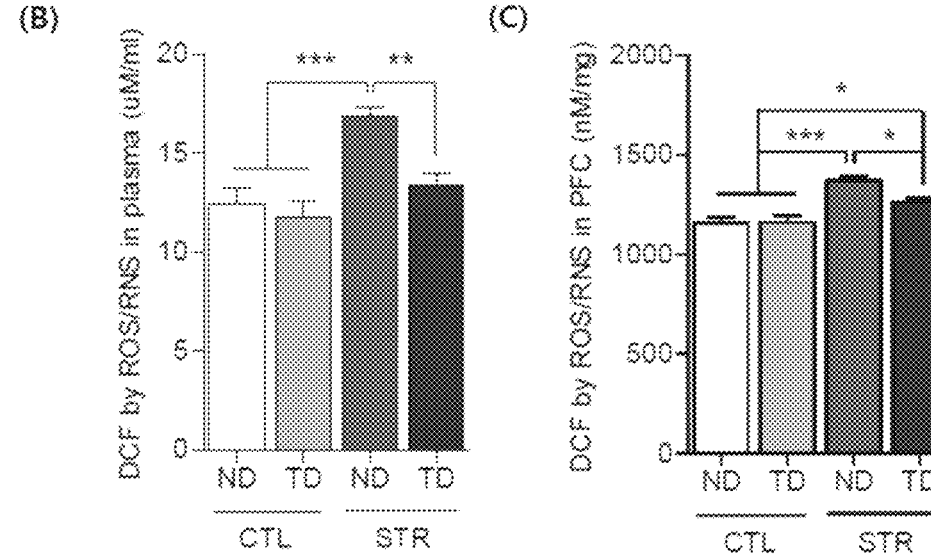

After that, the animal was sacrificed, and corticosterone amount in plasma was determined. As a result, it was found as illustrated in FIG. 4 that higher corticosterone amount is yielded due to stress. However, compared to the normal diet group of the stress group, it was found that there is a statistically significant decrease in corticosterone amount in the tyrosine diet group of the present invention (#, p<0.05). As a result of determining ROS/RNS both in plasma and PFC tissues, it was found that, compared to the normal diet group of the stress group, there is a statistically significant decrease in ROS/RNS in the tyrosine diet group (**: p<0.01, *: p<0.05).

Figure 5:
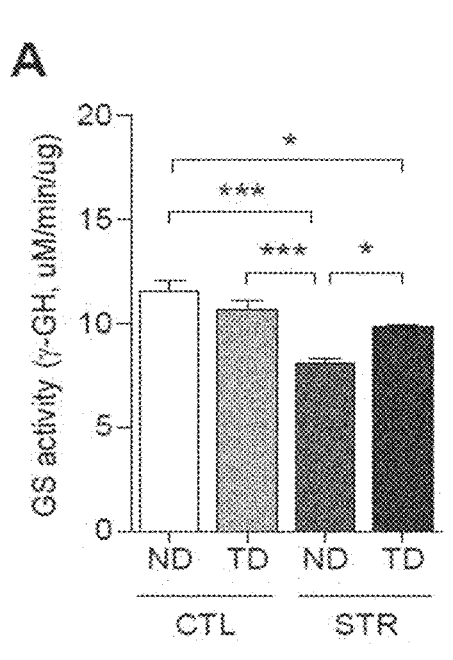
FIG. 5 shows the result of determining, in PFC from the chronic immobilization stress group (STR), which has been fed with tyrosine-diet (TD), (A) activity of GS, (B) expression amount of GS, and (C) nitration level of tyrosine included in GS.
Figure 5:
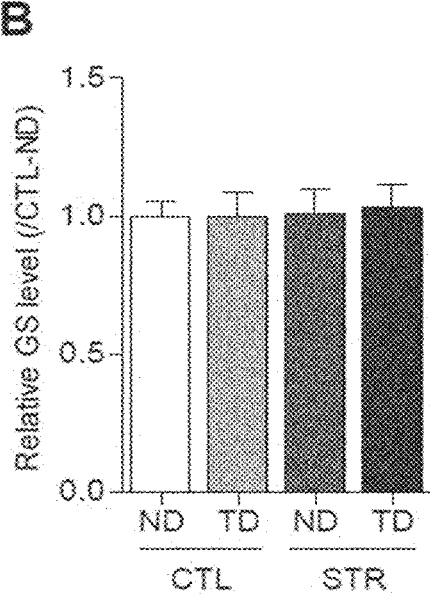
Figure 5:
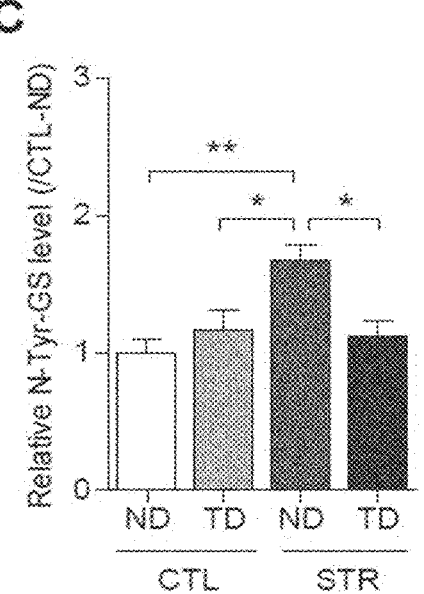
Figure 5:
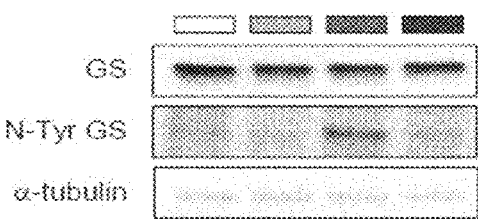

Meanwhile, when compared to the control group, the expression amount of glutamine synthetase (GS) was found to be similar between the normal diet group (ND) of the stress group and tyrosine diet group (TD), while lower GS activity was obtained due to the stress. It was found that, compared to the normal diet group of the stress group, there is a statistically significant increase in the GS activity in the tyrosine diet group and a statistically significant increase in the amount of N-Tyr (nitrated tyrosine) in GS. However, in the tyrosine-diet group, there is a statistically significant decrease in the amount of N-Tyr compared to the stress group with normal diet (FIG. 5).

Example 3. Determination of Amount of Glutamate, Glutamine, Tyrosine, and GABA in PFC from Chronic Immobilization Stress Group (STR) Fed with Tyrosine-Diet (TD)

The Amount of amino acids (glutamate, glutamine, tyrosine) and GABA in the PFC was quantified by liquid chromatography analysis (LC-MS/MS).

PFC tissues were lysed first, and the tissue supernatant was collected and diluted with internal reference (L-Glu-d5) and mobile phase. The diluted sample was divided into 5 samples and injected to LC-MS/MS system (Agilent 6460). As for the column, SeQuant ZIC®-HILIC column (2.1×100 mm, 3.5 μm, 100 Å) was used, and, as a mobile phase, acetonitrile containing 0.1% formic acid was used, and the separation was made by using concentration gradient.

For detecting the amino acids, multiple reaction monitoring and detection method was employed (m/z of Glu: 148→84, m/z of Gln: 147→84, m/z of GABA: 104→87, and m/z of internal reference: 153→88).

Figure 6:
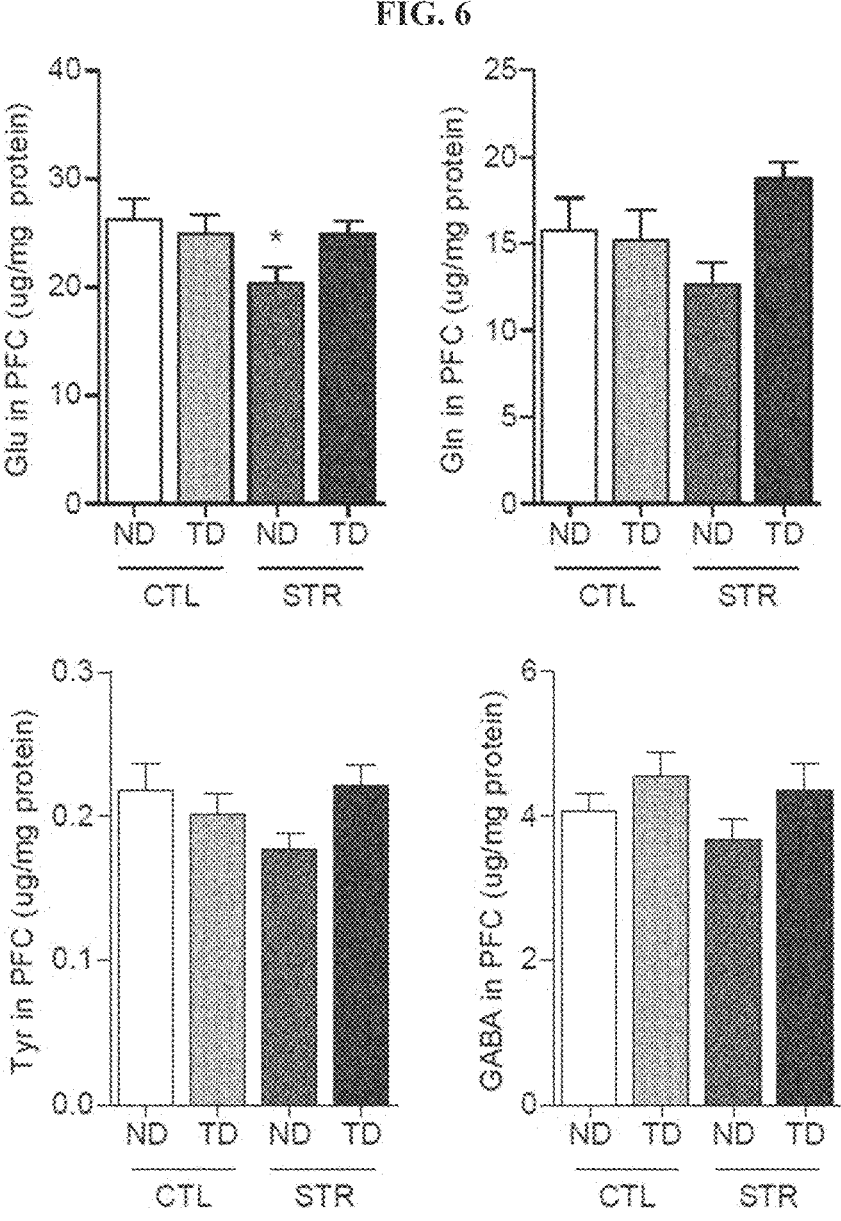
FIG. 6 shows the result of determining the amount of glutamate, glutamine, tyrosine, and GABA in PFC from the chronic immobilization stress group (STR), which has been fed with tyrosine-diet (TD).

As a result, it was found as illustrated in FIG. 6 that the normal diet group of the stress group has less amount of glutamate, glutamine, tyrosine and GABA in PFC compared to the normal group. On the other hand, the tyrosine diet group was found to have the amount of glutamate, glutamine, tyrosine and GABA that is higher than the amount level of the normal group.

Example 4. Change in Ammonia Amount in PFC of Chronic Immobilization Stress (CIS)-Induced Group (STR) Fed with Tyrosine-Diet (TD)

PFC tissues were weighed at a temperature of not more than −20° C. to prevent them from melting. To a 1.5 ml tube, RIPA (proteinase inhibitor cocktail, containing PIC) in an amount of 100 µl per 10 mg of the tissues and suitable number of glass beads were added, and then the tissues were lysed twice for 30 seconds by using a bullet blender. Lysed tissues were spun down, transferred to a fresh 1.5 ml tube, and then subjected to tissue homogenization for 1 min by ultrasonication. After centrifuged for 15 minutes at 12,000 rpm, supernatant was transferred to a fresh 1.5 ml tube and kept at −80° C. until use. With regard to those processes, every process except the weighing of PFC tissues was carried out at 4° C. Ammonia reference solution provided in Ammonia assay kit (Sigma-Aldrich, Cat Num. AA0100, provided at 10 µg/ml=588 µM) was diluted with water to prepare them at concentrations of 0 (blank control), 0.2, 0.4, 0.6, 0.8, and 1.0 µg/ml. Lysed PFC tissues were diluted by a factor of 2 using PBS buffer solution.

To 100 µl of the ammonia assay reagent provided in the Ammonia assay kit, 10 µl of the sample diluted by a factor 2 using PBS buffer solution (i.e., corresponding to 5 µg tissues) were added and incubated for 5 minutes at room temperature. At the same time, to 100 µl of the ammonia assay reagent, 10 µl of the reference solution were added and incubated for 5 minutes at room temperature. To calibrate the interference effect of the buffer solution for lysed PFC tissues (i.e., RIPA+PIC), RIPA+PIC diluted by a factor of 2 was used as a buffer solution blank control. After 5 minutes, absorbance was measured at 340 nm by using a microreader ($A_{initial}$).

After adding 10 µl of glutamate dehydrogenase solution and incubation for 5 minutes at room temperature, absorbance was measured at 340 nm by using a microreader ($A_{final}$).

DA340 nm ($A_{final}$-$A_{initial}$) was then calculated, and DA340 nm of the blank control or DA340 nm of buffer solution blank control was excluded by subtraction for the reference and sample, respectively.

By using the result value of references, linear regression is carried out and ammonia concentration in the sample was calculated by using it.

Figure 7:
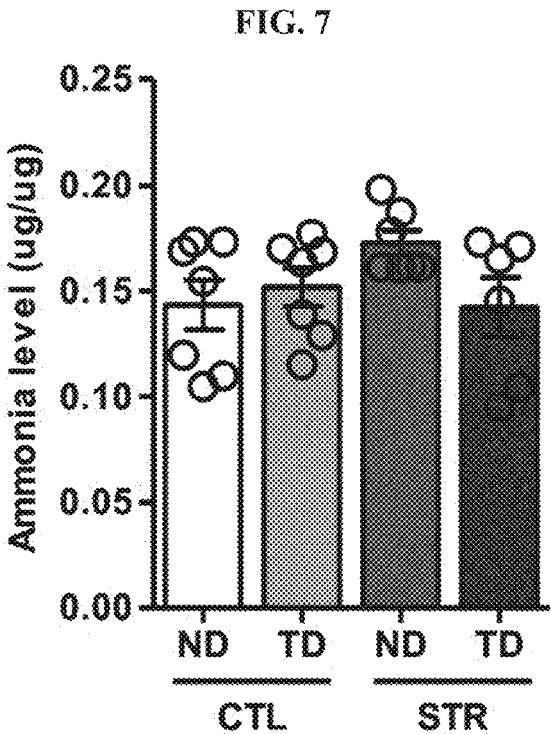
FIG. 7 shows the result of determining the amount of ammonia in PFC from the chronic immobilization stress group (STR), which has been fed with tyrosine-diet (TD).

As a result, it was found as illustrated in FIG. 7 that the stress group with normal diet has higher ammonia amount than the normal group. However, the tyrosine-diet group of the present invention showed the ammonia amount that is reduced to a similar level to the normal group.

Example 5. Analysis of Inhibitory Effect on In Vitro Nitration

Figure 8:
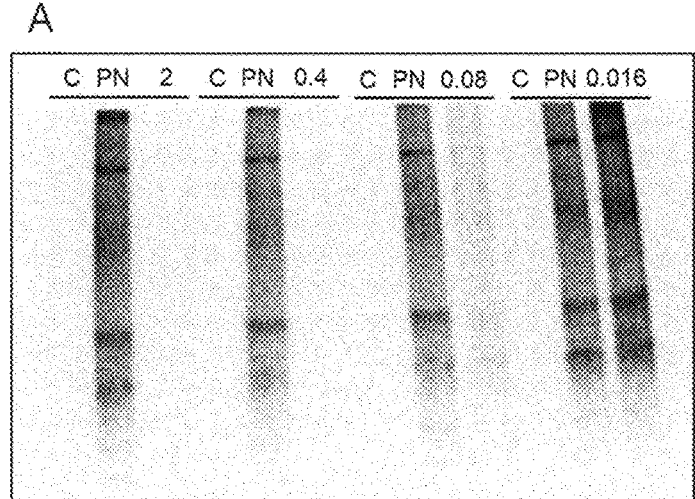
FIG. 8 shows the result of determining the inhibitory or denitration effect of tyrosine on nitration after mouse PFC protein is induced to undergo nitration by a treatment with $ONOO^-$.

By treating mouse PFC protein with ONOO⁻, protein nitration was induced and the inhibitory effect on nitration by tyrosine was examined. As a result, it was found as shown in FIG. 8 that nitration of the proteins is inhibited in tyrosine concentration dependent manner. The inhibitory effect on nitration was found to be at a similar level between L-tyrosine and D-tyrosine.

Furthermore, the inhibitory effect of tyrosine of the present invention on nitration was analyzed by using a lysate of mouse brain and liver tissues. Prefrontal cortex (PFC) tissues and liver tissues were separately collected from a mouse anesthetized with $CO_2$ gas. After weighing, the tissues were lysed using a tissue homogenizer. After centrifuge for 20 minutes at 4° C., 12,000 rpm, the supernatant was collected to give a lysate of PFC and liver tissues. To the tissue lysate, peroxynitrite (PN) for inducing protein nitration was added. After adding each of glutamine (Q), L-tyrosine ($_L$-Y) and D-tyrosine ($_D$-Y) at concentration 2 mM, the mixture was vortexed for 5 seconds and the reaction was allowed to occur for 10 minutes on ice. After that, Western blot was carried out by using anti-nitrotyrosine antibody (1:1,000), anti-glutamine synthetase antibody (1:5,000), anti-insulin receptor beta antibody (1:1,000), or anti-phosphorylated insulin receptor beta antibody (1:1,000).

Figure 9A:
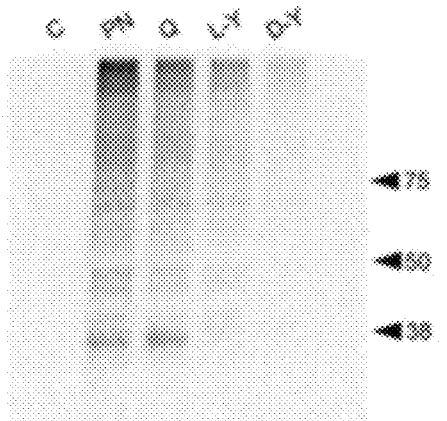
FIGS. 9A to 9D show the result of determining the inhibitory or denitration effect of L-tyrosine (L-Y) and D-tyrosine (D-Y) on nitration of brain and liver proteins, including (A) the Western blot result of nitrotyrosine protein in tissues of prefrontal cortex (PFC), (B) the Western blot result of nitrotyrosine protein in liver tissues, (C) the Western blot result of glutamine synthetase protein in tissues of prefrontal cortex (PFC), and (D) the Western blot result of glutamine synthetase, insulin receptor beta, and phosphory-lated insulin receptor beta in liver tissues.
Figure 9B:
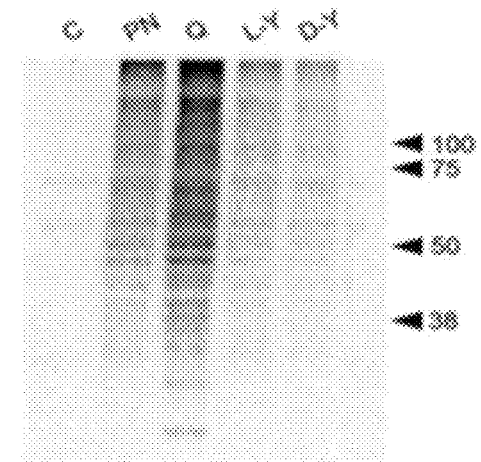
Figure 9C:
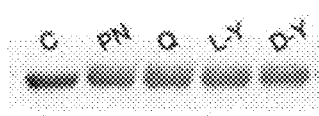
Figure 9D:
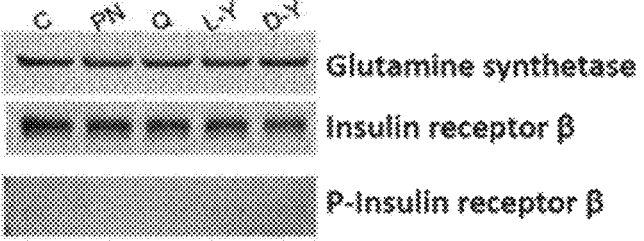

It was found as a result that, in the PFC and liver tissues, there are more proteins with high tyrosine nitration due to PN, and higher nitration of various proteins other than glutamine synthetase (GS) and insulin receptor beta subunit (IRβ) was found as a result of Western blot showing many bands. With regard to the proteins with high tyrosine nitration due to PN, it was also found that the nitration can be reduced by a treatment of a protein having tyrosine (Y) at the protein terminal (FIGS. 9A and 9B). Based on the expression result of GS and IRβ, it was found that there is no difference in protein amount between each treatment group of PFC and liver tissues. However, it was also found from Western blot of phosphorylated-IRβ (IRβ-p) that IRβ is nitrated by PN to yield fewer number of IRβ in phosphorylated form (FIGS. 9C and 9D).

Example 6. Determination of Effect of L-Tyrosine for Enhancing Insulin Sensitivity in High-Fat Diet Mouse Model of Type 2 Diabetes

(1) Establishment of High-Fat Diet Mouse Model of Type 2 Diabetes

Twenty-seven C57BL/6 male mice (3-week old) were acclimated to the breeding condition for 1 week. The animals were then divided into 3 groups and each group was supplied with normal diet (ND; 10 kcal % fat, calorie of 3.85 cal/g), high fat diet (HFD; 60 kcal % fat, calorie of 5.24 kcal/g), or high fat diet with L-tyrosine (L-Tyr) (HFD+L-Tyr; containing 181 mg of L-tyrosine/kg). The animals were allowed to have free access to water and animal feeds, and the bodyweight and food intake amount were measured every other day for 3 months. Blood glucose was measured every week.

Figure 10:
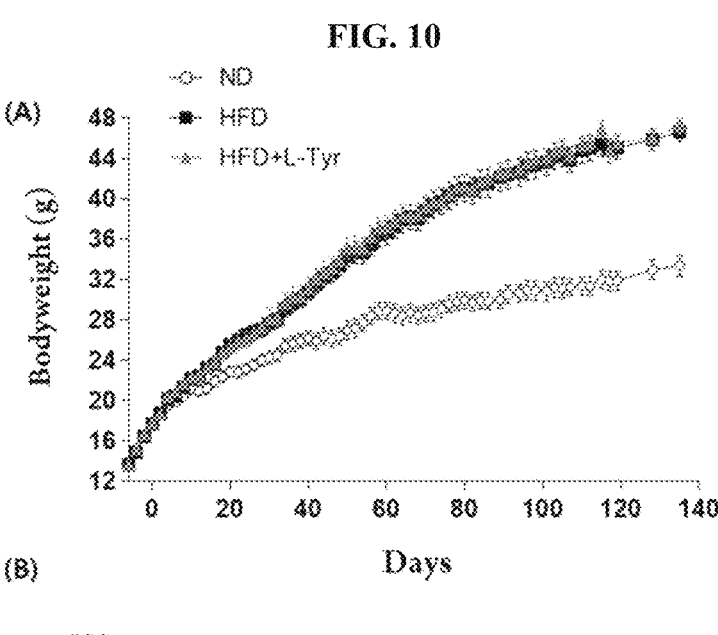
FIG. 10 shows the result of determining, for each different time period, (A) a change in bodyweight, (B) blood glucose, and (C) feed intake amount after L-tyrosine (L-Tyr) feeding to a mouse model, which has been induced to have type 2 diabetes by high-fat diet. * indicates that there is a statistically significant increase in blood glucose amount in the high-fat diet group (HFD) compared to the normal diet group (ND), in which * has $p<0.001$. #and ##indicate that there is a statistically significant decrease in blood glucose amount in the L-tyrosine containing diet group (HFD+L-Tyr) compared to the high-fat diet group (HFD), in which #has $p<0.05$ and ##has $p<0.01$.
Figure 10:
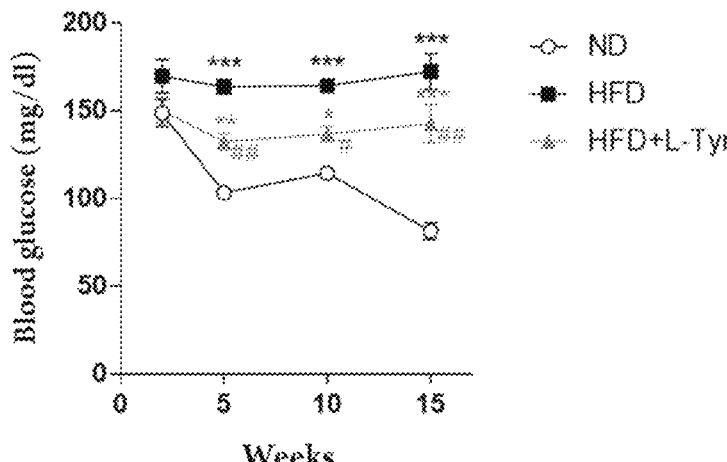
Figure 10:
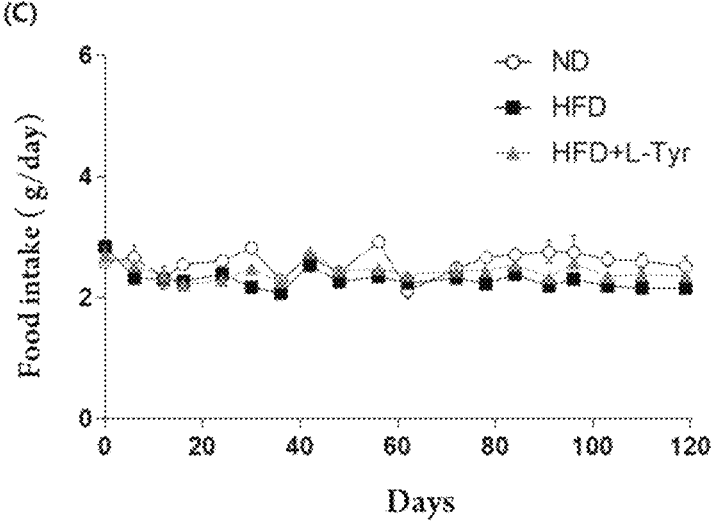

As a result, it was found as illustrated in FIG. 10 that there is a gradual increase in bodyweight. It was also found that, on the same test day, the HFD and HFD+L-Tyr groups have higher bodyweight than the ND group, and the bodyweight change appears to be similar between the HFD group and HFD+L-Tyr group. In terms of the food intake amount, there was almost no difference among different test groups, and also no difference was shown between different test time periods. In terms of the blood glucose, a statistically significant increase was obtained from the HFD group compared to the normal diet group (ND), and a statistically significant decrease was obtained from the HFD+L-Tyr group compared to the HFD group.

(2) Glucose Tolerance Test

D-glucose was dissolved in 1×PBS to prepare 40% D-glucose solution. Blood glucose of a mouse, which has been subjected to fasting for 16 hours, was measured, and, for having intraperitoneal injection of glucose in an amount of 2 g per 1 kg bodyweight, the animal was intraperitoneally injected with the glucose solution according to the following Formula (1).

Glucose injection amount(µl)=Bodyweight(g)×5    Formula (1)

For example, for a mouse with bodyweight of 45 g, 225 µl of 40% glucose solution were injected. After the intraperitoneal injection of glucose solution, blood glucose was measured at time points of 30, 60, 90 and 120 minutes.

Figure 11:
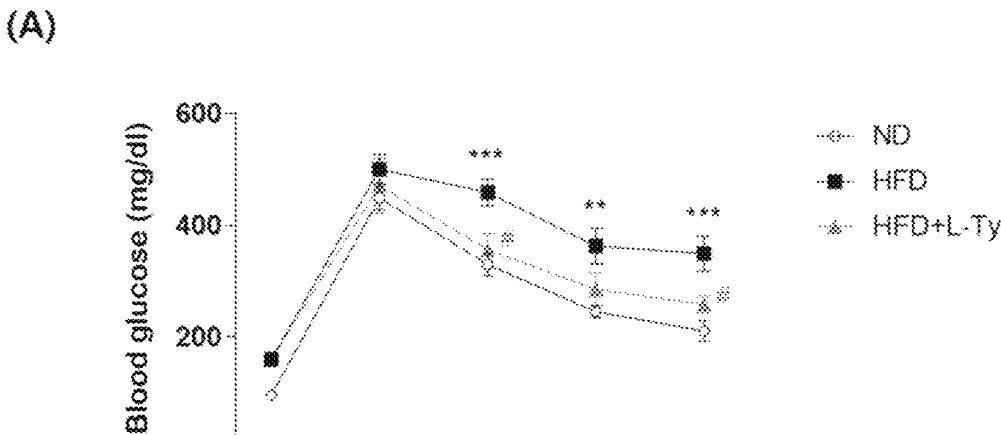
FIG. 11 shows the result of determining the glucose tolerance of a mouse fed with L-tyrosine, in which the mouse is a mouse model of type 2 diabetes induced by high-fat diet, including (A) the blood glucose amount over time, and (B) the area under curve of (A).  and * indicate that there is a statistically significant increase in blood glucose amount in the high-fat diet group (HFD) compared to the normal diet group (ND), in which  has $p<0.01$ and * has $p<0.001$. #indicates that there is a statistically significant decrease in blood glucose amount in the L-tyrosine containing diet group (HFD+L-Tyr) compared to the high-fat diet group (HFD), in which #has $p<0.05$.
Figure 11:
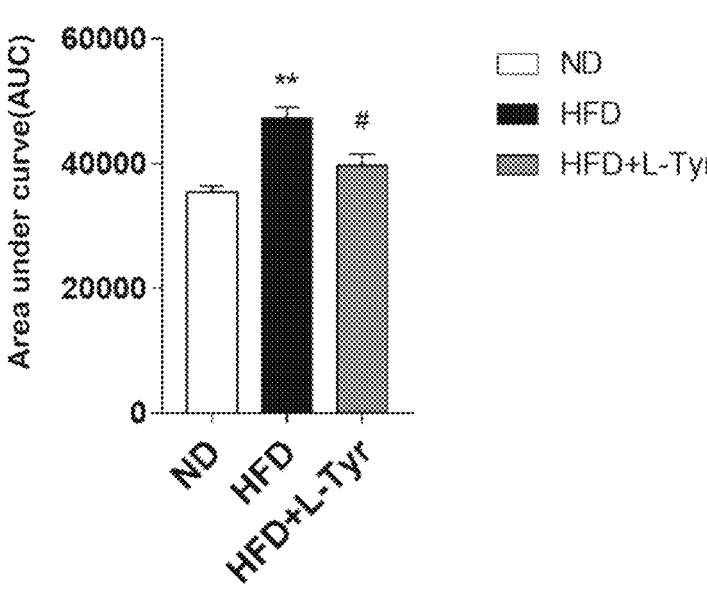

As a result, it was found as illustrated in FIG. 11 that a statistically significant increase in blood glucose was obtained from the high fat diet (HFD) group compared to the normal diet group (ND), while a statistically significant decrease in blood glucose was obtained from the high fat diet with L-tyrosine (L-Tyr) group of the present invention (HFD+L-Tyr).

(3) Insulin Resistance Test

Insulin was diluted with physiological saline to prepare 0.15 U/ml solution. Blood glucose of a mouse, which has been subjected to fasting for 6 hours, was measured, and the animal was intraperitoneally injected with insulin (0.75 U/bodyweight (kg)). After the intraperitoneal injection of insulin, blood glucose was measured at time points of 15, 30, 60, and 90 minutes.

Insulin injection amount(µl)=Bodyweight(g)×5    Formula (2)

Figure 12:
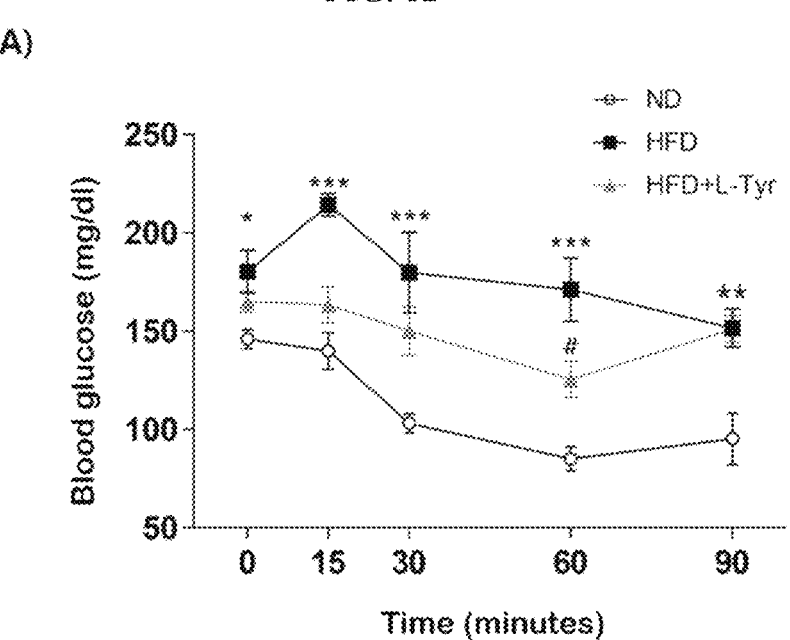
FIG. 12 shows the result of determining the insulin resistance of a mouse fed with L-tyrosine, in which the mouse is a mouse model of type 2 diabetes induced by high-fat diet, including (A) the blood glucose amount over time, and (B) the area under curve of (A). *, , and * indicate that there is a statistically significant increase in blood glucose amount in the high-fat diet group (HFD) compared to the normal diet group (ND), in which * has $p<0.05$,  has $p<0.01$, and * has $p<0.001$. #indicates that there is a statistically significant decrease in blood glucose amount in the L-tyrosine containing diet group (HFD+L-Tyr) compared to the high-fat diet group (HFD), in which #has $p<0.05$.
Figure 12:
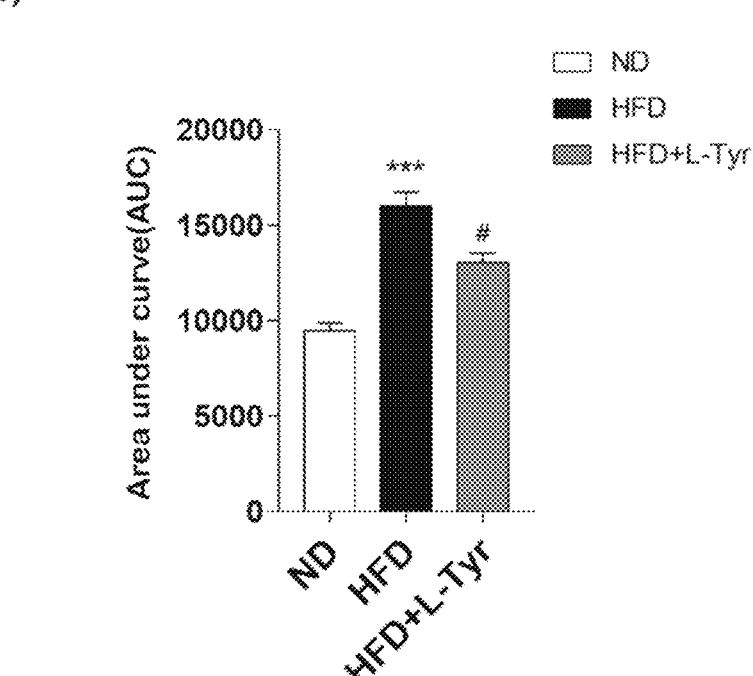

As a result, it was found as illustrated in FIG. 12 that a statistically significant increase in blood glucose amount was obtained from the high fat diet (HFD) group compared to the normal diet group (ND), while a statistically significant decrease in blood glucose amount was obtained from the high fat diet with L-tyrosine (L-Tyr) group of the present invention (HFD+L-Tyr).

(4) Determination of Change in Fat Accumulation in Tissues and Change in ROS/RNS Amount in Plasma Mouse was anesthetized with avertin, and blood was collected from a heart. After the reaction with EDTA in a vacucontainer, the blood was centrifuged for 15 minutes at 1,500×g, 4° C. to separate plasma. According to heart perfusion with PBS and 4% paraformaldehyde (PFA), tissue fixation was carried out. Then, each tissue was harvested and stored in PFA.

After 3-fold dilution of the plasma in PBS, concentration of reactive oxygen/reactive nitrogen (ROS/RNS) in plasma was measured using Oxiselect ROS/RNS assay kit (Cell Biolabs) according to the recommended experimental protocol.

Figure 13:
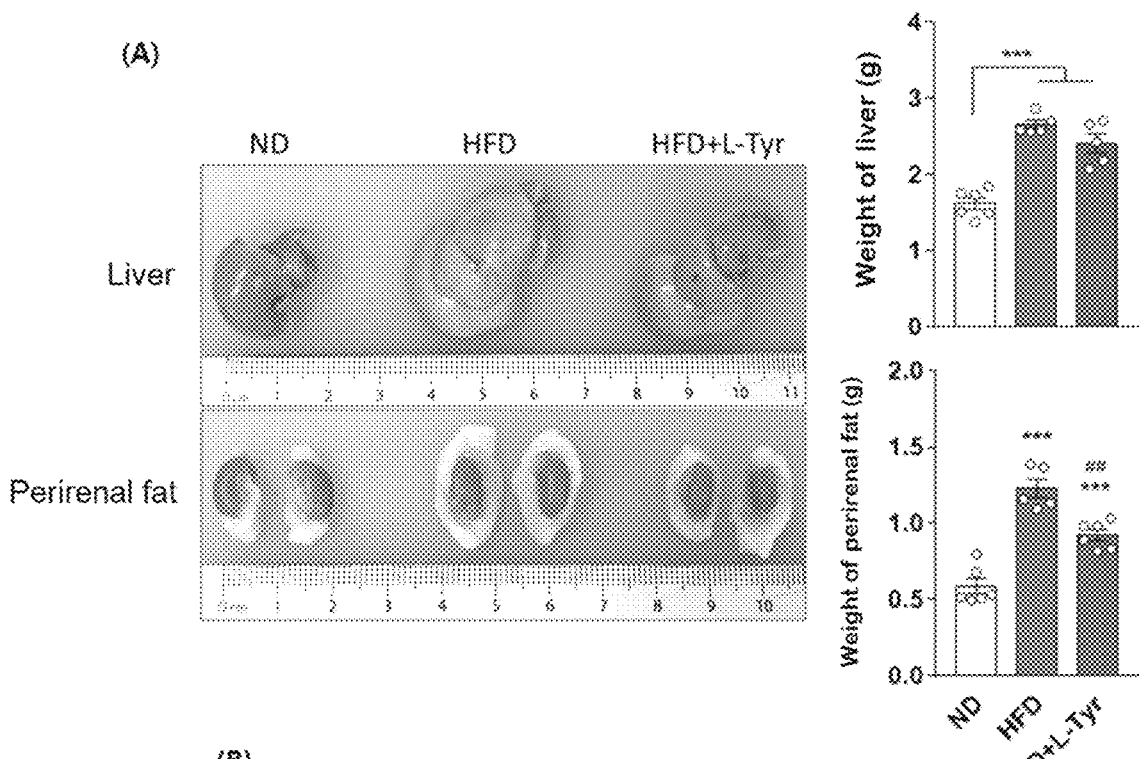
FIG. 13 shows the result of determining (A) a change in fat accumulation in tissues and (B) a change in ROS/RNS amount in plasma. * indicates that there is a statistically significant increase in tissue weight and ROS/RNS amount in plasma of HFD or HFD+Tyr compared to ND, in which * has $p<0.001$. #and ##indicate that there is a statistically significant decrease in tissue weight and ROS/RNS amount in plasma of HFD+Tyr compared to HFD, in which #has $p<0.05$ and ##has $p<0.01$.
Figure 13:
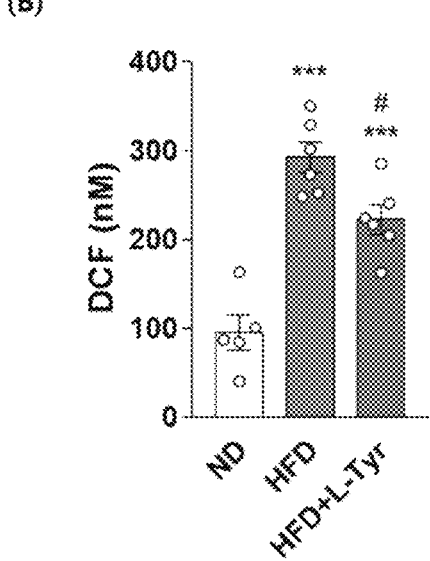

As a result, it was found that fat accumulation is reduced all over the liver by tyrosine and the amount of fat tissues around kidney is reduced to a statistically different level in the HFD animal model. A statistically significant increase in plasma ROS/RNS level was obtained from the high fat diet (HFD) group compared to the normal diet group (ND), while a statistically significant decrease in plasma ROS/RNS level was obtained from the high fat diet with L-tyrosine (L-Tyr) group of the present invention (HFD+L-Tyr) (FIG. 13).

Example 7. Determination of Inhibitory Effect of L-Tyrosine on Excitotoxicity and Oxidative Stress in Mouse Model of Epileptic Seizure which has been Induced to have Seizure by Kainic Acid By using a mouse model of epileptic seizure which has been induced to have seizure by kainic acid (KA), the inhibitory effect of tyrosine on glutamate excitotoxicity was determined. Kainic acid was intraperitoneally injected to the animals which have been fed with tyrosine for 7 days, each animal fed with different amount of tyrosine, and then the severity of seizure was examined.

(1) Epileptic Seizure

4-Week old male ICR mouse was provided for 1 week with normal diet or diet containing L-tyrosine, and it was allowed to have free access to water and feed.

Normal diet (ND): AIN-93G

1×L-Tyr: AIN-93G containing 181 mg/kg L-Tyr

3×L-Tyr: AIN-93G containing 543 mg/kg L-Tyr

5×L-Tyr: AIN-93G containing 905 mg/kg L-Tyr

Kainic acid (KA, Abcam) was dissolved in physiological saline in hot water bath to prepare 9 mg/ml kainic acid solution. After intraperitoneal injection of kainic acid (30 mg/kg), severity level and symptoms of seizure were recorded for 2 hours. Severity level of seizure was decided based on the criteria given in the following Table 2, and also the bodyweight was measured before and 24 hours after the injection of kainic acid, and then the results are compared to each other.

Furthermore, raw brain tissues of a mouse survived 24 hours after the injection of kainic acid were either directly removed, or, removed after tissue fixation by PFA perfusion.

TABLE 2

| Key symptoms of each seizure level | |
| --- | --- |
| Level | Key Symptoms |
| I | Sit or stay still in the corner, eyes focused |
| II | Stretched body, tight and rigid tail, ears held back, and bulged red eyes |
| III | Repeated head twitching, sit with front paws on stomach |
| IV | Running and jumping with intermittent seizure, remain calm, sit and lie due to tonic-clonic seizure |
| V | Continuous seizure at level V |
| VI | Intermittent body seizure, not much of continuous body balance using paws, and mostly dead |

Figure 14:
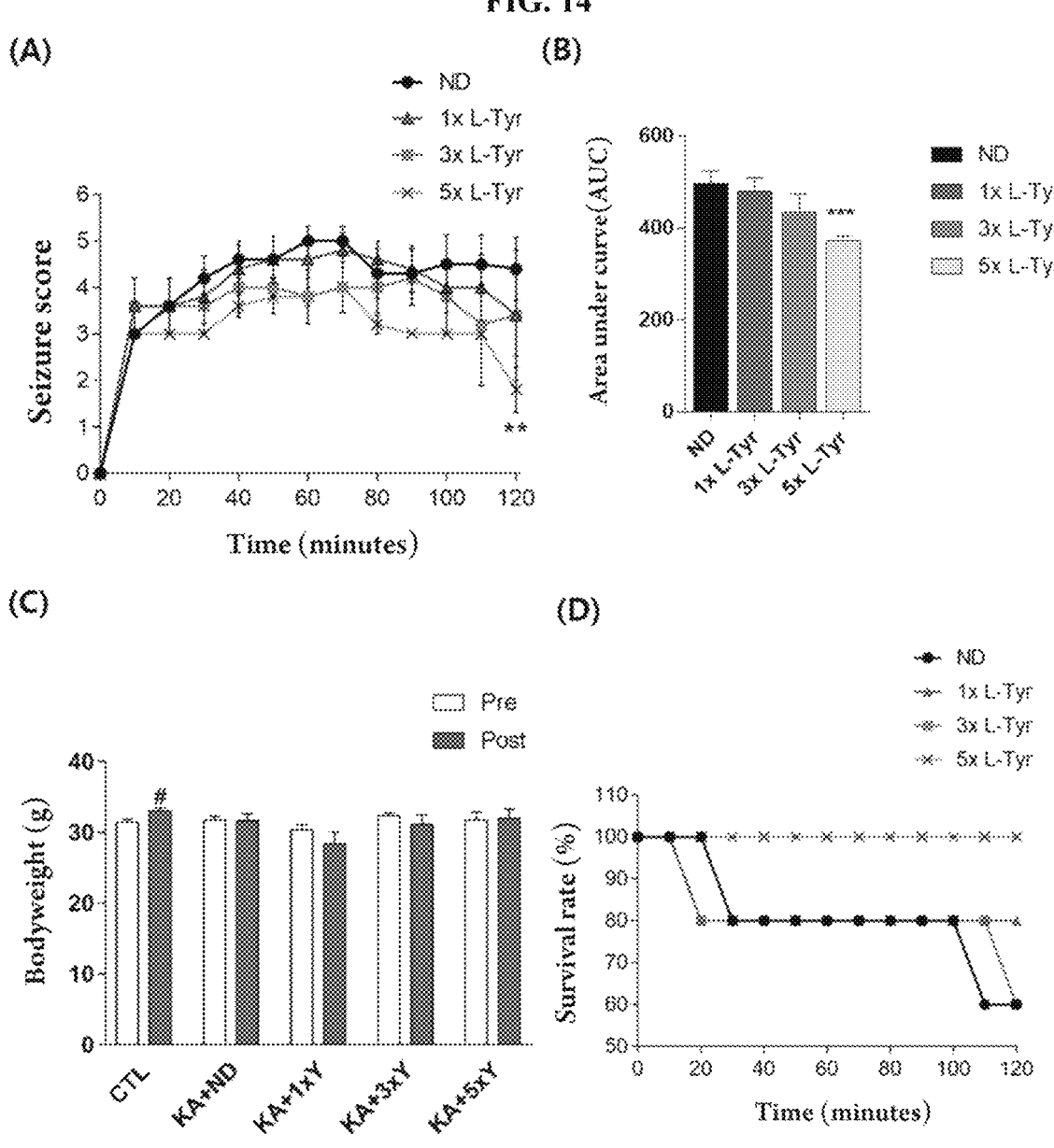
FIG. 14 shows the result of determining (A) a change in seizure level, (C) a change in bodyweight, and (D) survival rate after tyrosine diet, and the area under curve of (A) is shown in (B).  and * indicate that there is a statistically significant decrease in seizure level in 5×L-Tyr compared to ND, in which  has $p<0.01$ and * has $p<0.001$. #indicates that there is an increase in bodyweight of CTL compared to the bodyweight before seizure, in which #has $p<0.05$.

As a result, it was found that the severity of seizure is gradually reduced depending on tyrosine amount, and there was no difference in bodyweight among different test groups (FIG. 14). Furthermore, in case of an animal having no tyrosine diet, there was an animal perished before 120 minutes due to strong seizure phenomenon caused by kainic acid. However, a phenomenon showing an improvement in mouse death was also observed depending on intake amount of tyrosine. In case of the diet with feeds containing tyrosine in an amount of 900 mg/kg (actual intake amount), all of the mice have survived.

(2) Measurement of ROS/RNS

Hippocampus in brain tissues was added with RIPA (containing proteinase/phosphatase inhibitor), in an amount of 100 µl per 10 mg of the tissues, and then lysed for 1 minute by using glass beads and a bullet blender. Supernatant was separated by centrifuge for 15 minutes at 12,000×g, 4° C., and, after 10-fold dilution with PBS, used for measurement of ROS/RNS. Concentration of ROS/RNS was measured by using Oxiselect ROS/RNS assay kit (Cell Biolabs) according to the recommended experimental protocol.

Figure 15:
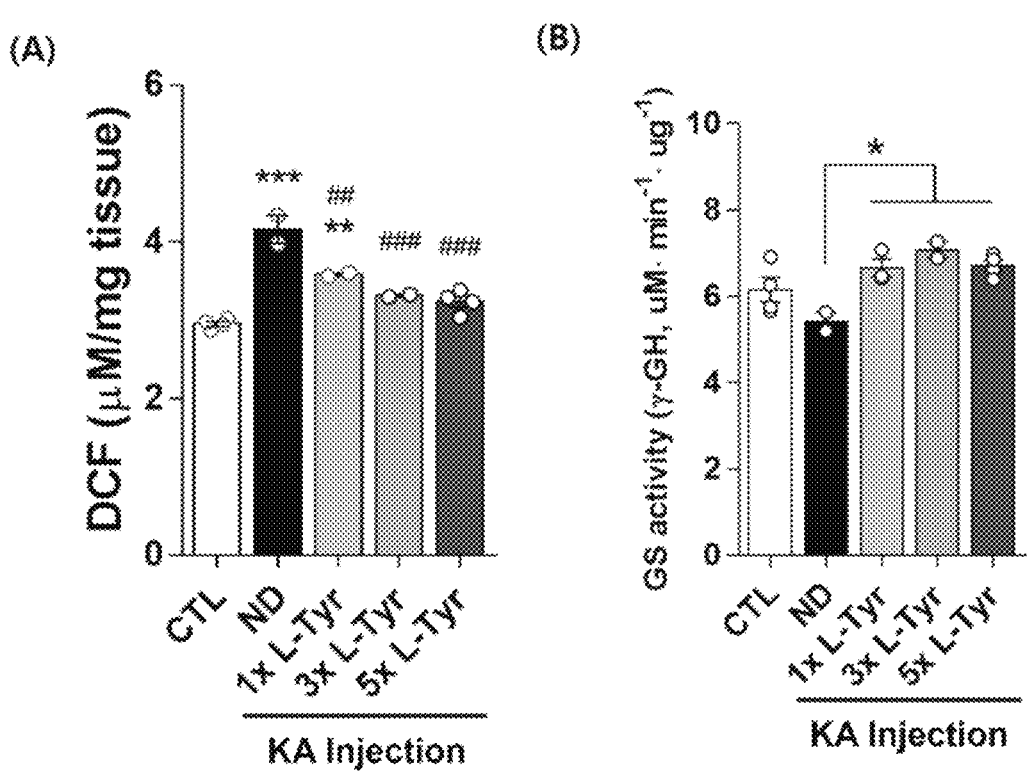
FIG. 15 shows the result of determining (A) a change in the amount of ROS/RNS and GS activity in hippocampal tissues of a mouse which has survived after kainic acid (KA) treatment.  and * in (A) indicate that there is an increase in ROS/RNS amount compared to CTL, in which  has $p<0.01$ and * has $p<0.001$. ##and ###indicate that there is a statistically significant decrease in ROS/RNS amount in the tyrosine diet group compared to the ND group with normal diet after KA injection, in which ##has $p<0.01$ and ###has $p<0.001$. * in (B) indicates that there is a statistically significant increase in GS activity in the tyrosine diet group compared to the ND group with normal diet after KA injection, in which * has $p<0.05$.

As a result of analyzing a change in ROS/RNS amount and GS activity in hippocampal tissues of a mouse survived after the injection of kainic acid, it was found that higher amount of ROS/RNS is obtained due to kainic acid, but, in the mouse supplemented with tyrosine, the amount was reduced to the level of the control group (FIG. 15).

(3) Measurement of Activity of Glutamine Synthetase (GS)

To a 96-well plate, 2 μl of hippocampus lysate were added, and then adjusted to 50 μl by additionally adding 50 mM imidazole-HCl buffer solution (pH 6.8). After adding 50 μl of GS activity assay buffer solution (50 mM imidazole-HCl, pH 6.8, 25 mM L-glutamine, 12.5 mM hydroxylamine, 12.5 mM sodium arsenate, 1 mM MnCl$_2$ and 0.08 mM ADP), the reaction was allowed to occur at 37° C. for 30 to 60 minutes.

Upon the completion of the reaction, γ-glutamylhydroxamate as a reference material was added to an empty well such that it is present at a concentration of between 0.391 and 25.0 mM. To the sample and reference material, 100 μl of reaction termination solution (90 mM FeCl$_3$, 1.8 N HCl and 1.45% (w/v) trichloroacetic acid) were added and absorbance at a wavelength of 560 nm was measured.

Based on comparison with standard curve, GS activity was obtained for each sample. GS activity was expressed in terms of the production amount of γ-glutamylhydroxamate as a final product with unit of μM/min/μg of protein.

As a result, it was found as shown in FIG. 15 that lower GS activity is caused by kainic acid, but the mouse supplemented with tyrosine showed the activity that is the same or higher than the control group.

(4) Immunohistochemistry (IHC)

Blood perfusion with PBS and PFA was carried out through animal heart, and the brain was removed and post-fixed in PFA for 15 hours or longer. After washing 3 times for 10 minutes with PBS, brain tissue specimen with thickness of 40 μm was obtained using a vibratome.

In IHC buffer solution (PBS containing 0.3% Triton X-100) in which 3% bovine serum albumin is dissolved, the above-obtained brain specimen was blocked for 1 hour at room temperature and then reacted at 4° C. for 15 hours or longer with a primary antibody (anti-NeuN (Millipore, MAB377, 1:500), anti-Iba1 (Wako, 019-19741, 1:200)) (IHC buffer solution containing 3% BSA). After washing 3 times, each for 10 minutes, with the IHC buffer solution, it was reacted with a flurolabeled secondary antibody (anti-Mouse IgG Alexa Fluor 488 (Invitrogen, 1:1000), anti-Rabbit IgG AlexaFluor594 (Invitrogen, 1:000)) for 2 hours at room temperature (IHC buffer solution containing 3% BSA). After washing 3 times, each for 10 minutes, with the IHC buffer solution, the specimen was fixed on a silane-coated glass slide. An anti-fade solution containing DAPI was added onto the specimen and then dried after covering with a cover glass. Signal density of an image photographed with a fluorescent microscope was analyzed by using Image J analysis program.

Figure 16:
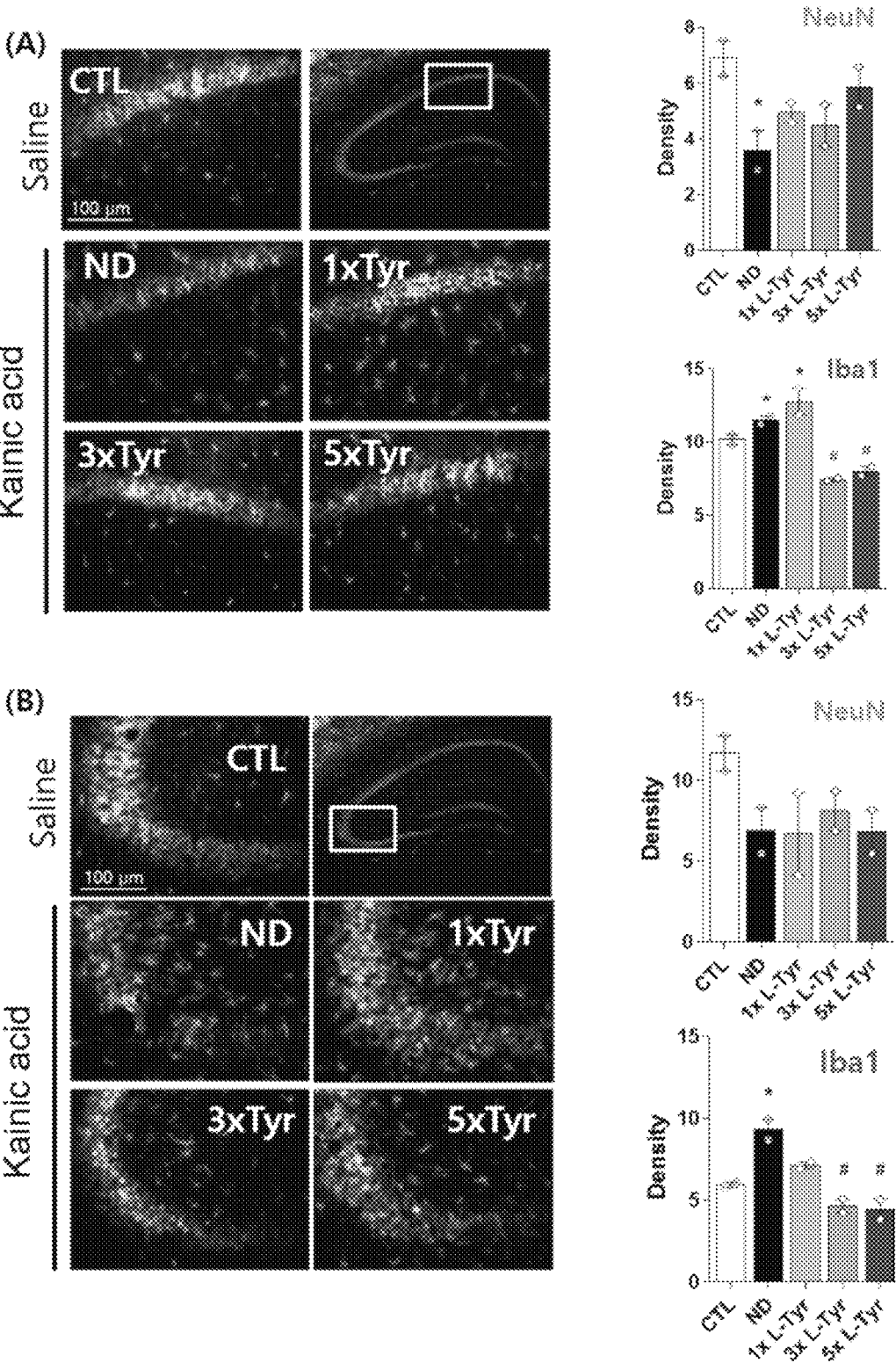
FIG. 16 shows the result of immunohistochemistry for analyzing the number of neurons and activity of microglia in hippocampal area (CA1(A), CA3(B)) after kainic acid (KA) treatment. * indicates that, compared to CTL, there is a lower number of neurons or higher activity of microglia which causes inflammation, in which * has $p<0.05$. #indicates that, in the tyrosine diet group, there is a significant decrease in the activity of microglia, in which #has $p<0.05$.

As a result of examining the brain tissue of a model mouse having seizure induced by kainic acid, it was found that number of the neuronal cells in hippocampal area (CA1, CA3) is reduced by kainic acid and higher activity of microglia is shown from the same area. However, when tyrosine is provided to the animal, number of the neuronal cells was maintained without a loss and the activity of microglia due to inflammatory response is reduced (FIG. 16).

Example 8. Determination of Effect of Preventing Cognitive Impairment by D-Tyrosine in a Mouse Model of Chronic Immobilization Stress

(1) Preparation of Mouse Model of Chronic Immobilization Stress

Twenty-eight C57BL/6 male mice (7-week old) were divided into two groups, each group provided for 1 week with a normal diet or D-tyrosine (D-Tyr)-containing diet (181 mg D-Tyr/kg AIN-93G). The animals were allowed to have free access to water and feeds, ant the bodyweight and food intake amount were measured two times per week.

Once the animals become 8-week old, they were applied with chronic immobilization stress (CIS) under light condition of 200 lux, 2 hours per day for 2 weeks. The animals were divided into the control group (CTL), D-Tyr diet control group (CTL+D-Tyr), chronic stress group (STR), and D-Tyr diet chronic stress group (STR+D-Tyr), in which each group consists of 7 animals.

(2) Cognitive Function Test

Upon the completion of the CIS for 2 weeks, a cognitive function test was carried out. To compare the cognitive function between the group provided with D-Tyr-containing diet over the entire test period including habituation period and normal feed diet group, an object recognition test (ORT) and an object location recognition test (OLT) for testing long-term memory skills were carried out.

ORT: The test consists of three stages, i.e., habituation, familiarization, and test. The animals were habituated in a test box, 10 minutes per day for 2 days. At the familiarization stage on Day 3, they were allowed to explore two identical objects for 10 minutes. At the time of introduction to a test box, the mouse was placed such that it faces an object-free wall. At the test stage on Day 4, one of the two objects was replaced with a new object. Then, the animal was allowed to explore for 10 minutes but only the record obtained from the initial 5 minutes were used as test data. The object recognition function index (i.e., discrimination index: DI) was calculated based on the following formula (3).

$$DI(\text{Discrimination Index}) = [\text{Time for exploring new object} - \text{Time for exploring familiar object}] / [\text{Time for exploring new object} + \text{Time for exploring familiar object}] \quad \text{Formula (3)}$$

OLT: 24 Hours after carrying out ORT, location of a familiar object was changed, and the animal was allowed to explore for 5 minutes. According to the same method as the aforementioned object recognition function index (DI), ratio of time spent for exploring an object with changed location compared to the entire time for exploring an object was calculated. Accordingly, object location recognition function index was obtained.

Figure 17:
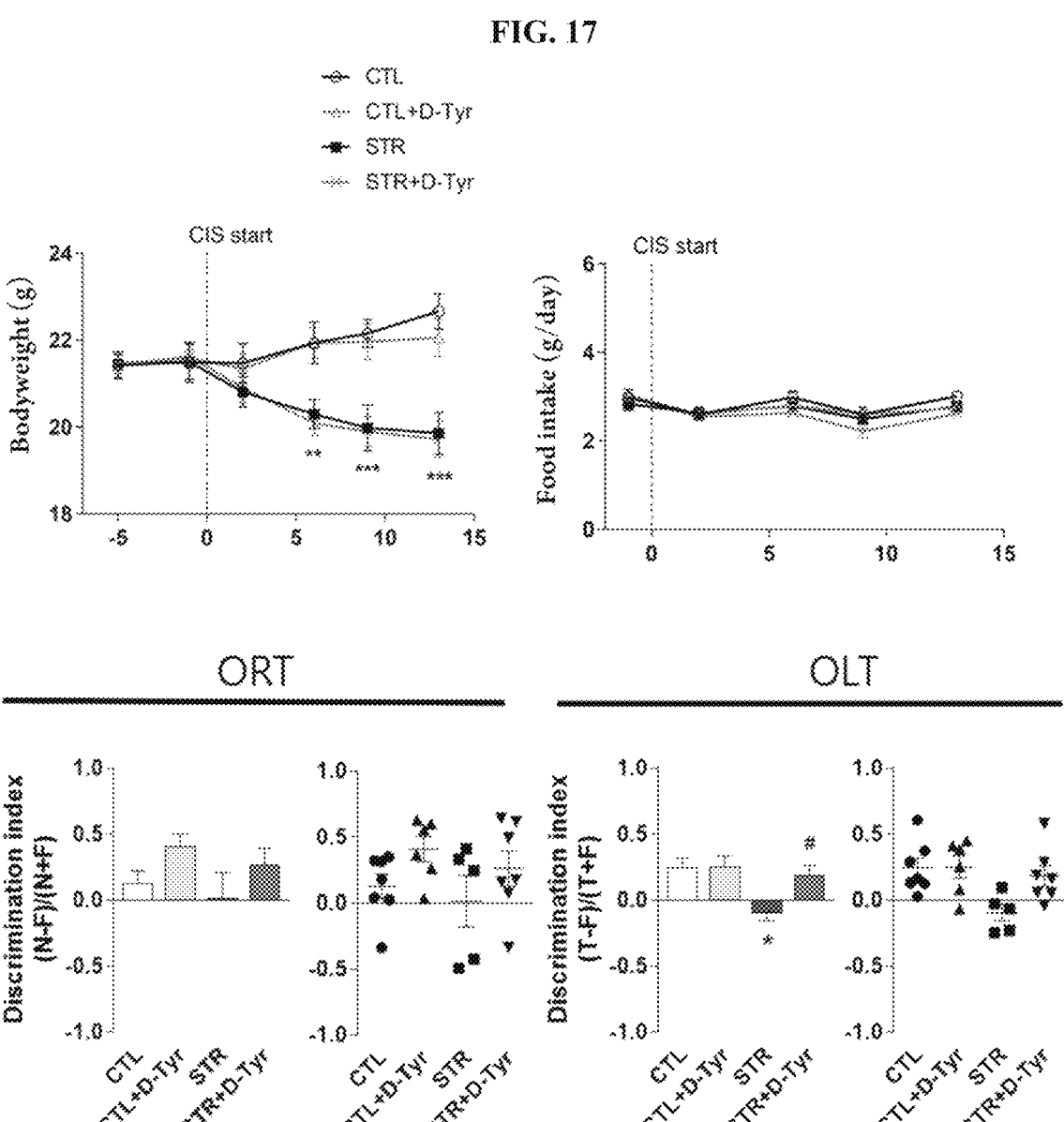
FIG. 17 shows the result of determining the effect of preventing cognitive impairment by D-tyrosine in a mouse model of chronic immobilization stress.

In order to determine the effect of protecting cognitive function by tyrosine using a mouse model of chronic immobilization stress having mild cognitive impairment, chronic stress was applied (for 14 days) while the animal was provided with feeds supplemented with tyrosine. As a result, it was found that the no difference in bodyweight and food intake amount is shown depending on the presence or absence of tyrosine, and no statistically significant difference is shown from ORT. Meanwhile, it was found according to OTL that, as a result of the intake of tyrosine, the cognitive function which has been impaired by stress can be maintained at the level of the control group (FIG. 17).

Example 9. Determination of Effect of L-Tyrosine for Reducing Brain Infarction and Oxidative Stress in Mouse Model of Stroke Using Endothelin-1

(1) Preparation of Mouse Model of Stroke

C57BL/6 male mouse (8-week old) was provided with normal diet or diet containing L-tyrosine for more than a week, and the animal was allowed to have free access to water and feeds Normal diet (ND): AIN-93G L-Tyr: AIN-93G containing 905 mg/kg L-Tyr

(2) Preparation of Endothelin-1 and Stereotaxic Surgery

To de-ionized water, endothelin-1 was added (2 μg/μl), and, after vigorous vortexing, completely dissolved by ultrasonication at 4° C. for about 10 minutes.

The mouse was anesthetized by intraperitoneal injection of avertin as an anesthetic (0.5 ml/25 g of mouse body-weight). Thereafter, endothelin-1 was injected (2 μg) to the cerebral motor cortex area (with bregma at the center, AP 1.5 mm, ML-1.5 mm, and DV 1.8 mm) by stereotaxic surgery. The injection was made at speed of 0.3 μl per minute. The needle was left for about 5 minutes after completing the injection so that endothelin-1 can be fully absorbed in animal tissues. After suturing the skin, the animal was allowed to recover in the original cage.

(3) Tissue Staining

Perfusion with PBS and PFA was carried out, via animal heart and the brain was removed and post-fixed in PFA for 15 hours or longer. After washing 3 times for 10 minutes with PBS, brain tissue specimen with thickness of 40 μm was obtained using a vibratome. Then, four specimens collected from the area injected with endothelin-1 were fixed on a silane-coated glass slide. The dried specimen was immersed in 0.1% cresyl violet solution for 5 minutes, and subsequently immersed twice in de-ionized water to remove the staining solution. After dehydration by immersion for 2 to 3 seconds in 100% ethanol, it was rinsed twice with xylene for 5 seconds. After applying the mount solution, the specimen was covered with a cover glass and dried. The stained specimen sample was observed under an optical microscope, and, with the stored image, the area showing brain infarction was calculated by using Image J analysis program.

(4) Measurement of Activity of Glutamine Synthetase (GS)

To a 96-well plate, 2 μl of lysate of cerebral motor cortex were added, and then adjusted to 50 μl by additionally adding 50 mM imidazole-HCl buffer solution (pH 6.8). After adding 50 μl of GS activity assay buffer solution (50 mM imidazole-HCl, pH 6.8, 25 mM L-glutamine, 12.5 mM hydroxylamine, 12.5 mM sodium arsenate, 1 mM MnCl$_2$ and 0.08 mM ADP), the reaction was allowed to occur at 37° C. for 30 to 60 minutes.

Upon the completion of the reaction, γ-glutamylhydroxamate as a reference material was added to an empty well (0.391 to 25.0 mM). To the sample and reference material, 100 μl of reaction termination solution (90 mM FeCl$_3$, 1.8 N HCl and 1.45% trichloroacetic acid) were added and absorbance at a wavelength of 560 nm was measured. Based on comparison with standard curve, GS activity was obtained for each sample. GS activity was expressed in terms of the production amount of γ-glutamylhydroxamate as a final product with unit of μM/min/μg of protein.

Figure 18:
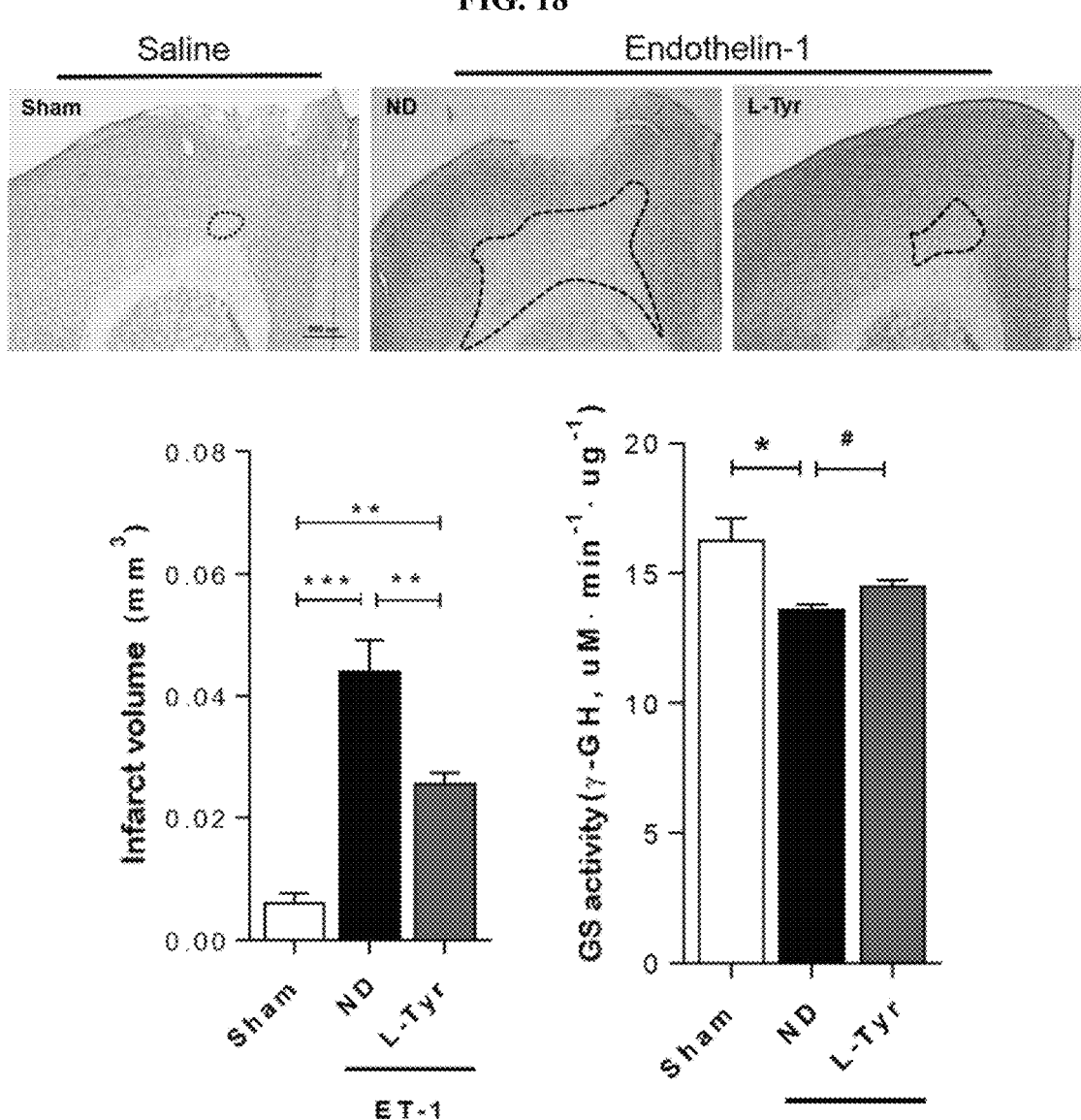
FIG. 18 shows the result of determining the effect of reducing brain infarction and enhancing GS activity by L-tyrosine in a mouse model of stroke that was made by endothelin-1.

As a result of the test in which vascular stroke was induced by injecting endotehlin-1 to cerebral motor cortex of a mouse, it was found that there is a huge increase in infarct volume in the test group administered with endothelin-1 compared to the control group administered with saline, while the infarct volume is reduced in the test group fed with tyrosine at an amount of 900 mg/kg (feed weight). It was also found that, although GS activity of the tissues is reduced by endotheline-1 compared to the control group, the activity can be maintained by Tyr diet (FIG. 18).

Example 10. Determination of Denitration Effect of Tyrosine on Human Recombinant MnSOD

1) Quantification of Peroxynitrite

Peroxynitrite was diluted by 40 times with 0.3 M NaOH, and absorbance at 302 nm was measured. Then, it was quantified by using the molar absorption coefficient of peroxynitrite) ($\varepsilon_{302}$=1670 M$^{-1}$ cm$^{-1}$).

2) Measurement of SOD Activity

For the measurement of SOD activity, SOD colorimetric activity kit by ThermoFisher was used. Human recombinant MnSOD within reference SOD range, peptide, and peroxynitrite were admixed with one another, and the reaction was allowed to occur on ice for 10 minutes. To a 96-well plate, 10 μl of reference SOD or the reaction mixture, and 50 μl of a substrate solution provided in the kit were added, and the absorbance at 450 nm was measured. After adding 25μl of xanthine oxidase provided in the kit and allowing the reaction to occur for 20 minutes at room temperature, absorbance at 450 nm was measured. By using the data obtained by subtracting the first-measured absorbance from the second-measured absorbance, SOD activity was obtained.

Figure 19:
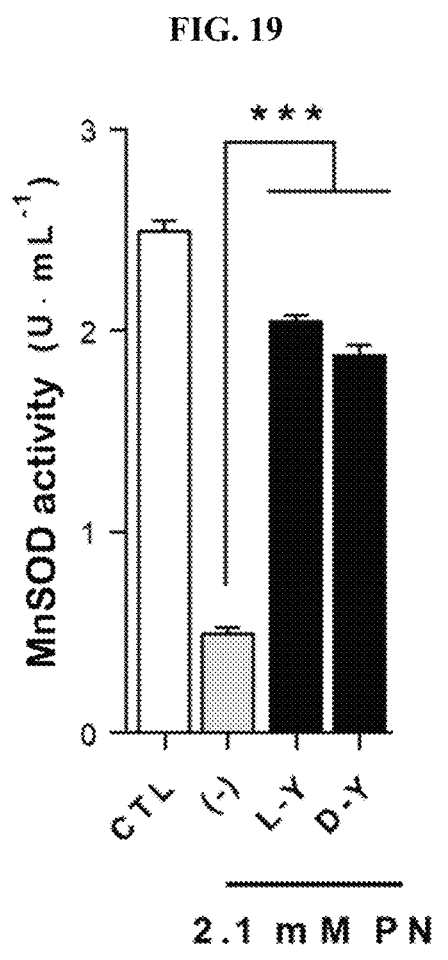

As a result, it was found that lower SOD activity is caused by active nitrogen species present in living body. It was also found that the activity of MnSOD is impaired by peroxynitrite while the SOD activity can be maintained by added Tyr (L-, D-form) (FIG. 19).

Example 11. Determination of Effect of Tyr on Acute Renal Failure

(1) Animal Test

C57BL/6 male mouse (23 to 25 g, KOATECH, South Korea) was allowed to have free access to diets and water in sterile breeding room with constant temperature and humidity. The animals were divided into 3 test groups, i.e., 1) Control group (Sham), 2) Renal ischemia having treatment with prepared solvent and induced reperfusion group (CMC+IR), and 3) Renal ischemia having treatment with L-tyrosine and induced reperfusion group (L-Tyr+IR).

L-Tyrosine (100 mg/kg) was suspended in 0.5% CMC (carboxymethyl cellulose). The animal was orally administered, once a day for 4 days, with L-tyrosine or the prepared solvent CMC. Thirty minutes after the oral administration on Day 4, renal ischemia was caused. Specifically, the animal abdomen was cut and renal pedicles at both sides were clamped using a Muller atraumatic vascular clamp to cause renal ischemia. After 25 minutes of blood ischemia, the clamp was removed followed by reperfusion. The control group (Sham) received the same operational procedures as above except the ischemia using clamp. Twenty-four hours after the reperfusion, the test animal was sacrificed, blood was collected from the heart, and the tissues were harvested.

(2) Plasma Creatinine

Blood collected in the above was centrifuged for 15 minutes at 3,000 rpm to separate plasma, and blood creatinine was measured by using Jaffe method. With regard to Jaffe method, based on a difference between the absorbance measured at a wavelength of 510 nm after the reaction of plasma sample with picric acid and the absorbance measured after completing the reaction using 60% acetic acid, the amount of creatinine was calculated and it was expressed in unit of mg/dl.

(3) Quantitative Real-Time Polymerase Chain Reaction

According to Trizol method, total RNA was extracted from kidney tissues, and cDNA was synthesized by using Revert Aid Reverse Transcription System (ThermoFisher). Quantitative PCR was carried out with CFX Connect Real-Time PCR system (Bio-Rad) by using iQ SYBR Green Super mix (Bio-Rad). As a housekeeping gene, GAPDH was used. Primers used for the experiment are disclosed in the following Table 3.

TABLE 3

| Gene | Di-rection | Primer Sequence (5'→3') | SEQ ID NO: |
|------|-----------|-------------------------|------------|
| IL-1β | Forward | TCGCAGCAGCACATCAACAAGAG | 1 |
| | Reverse | GGTGCTCATGTCCTCATCCTGGA | 2 |
| IL-6 | Forward | CCAATTCATCTTGAAATCAC | 3 |
| | Reverse | GGAATGTCCACAAACTGATA | 4 |
| NQO-1 | Forward | ATGACATCACAGGTGAGCTGAAGG | 5 |
| | Reverse | CTCAAACCAGCCTTTCAGAATGGC | 6 |
| GAPDH | Forward | GTGGCAAAGTGGAGATTGTTG | 7 |
| | Reverse | TTGACTGTGCCGTTGAATTTG | 8 |

(4) Western Blot

Kidney tissues were homogenized with RIPA buffer solution. After centrifuge for 15 minutes at 16,000×g, 4° C., supernatant was collected and the protein quantification was carried out by BCA method. After SDS-PAGE electrophoresis, proteins were transferred to a PVDF membrane, and then blocked with 5% skim milk. Following a reaction with nitro-tyrosine and β-actin primary antibody and corresponding secondary antibody, analysis was made with ChemiDoc XRS⁺ System (Bio-Rad) according to ECL method.

Figure 20:
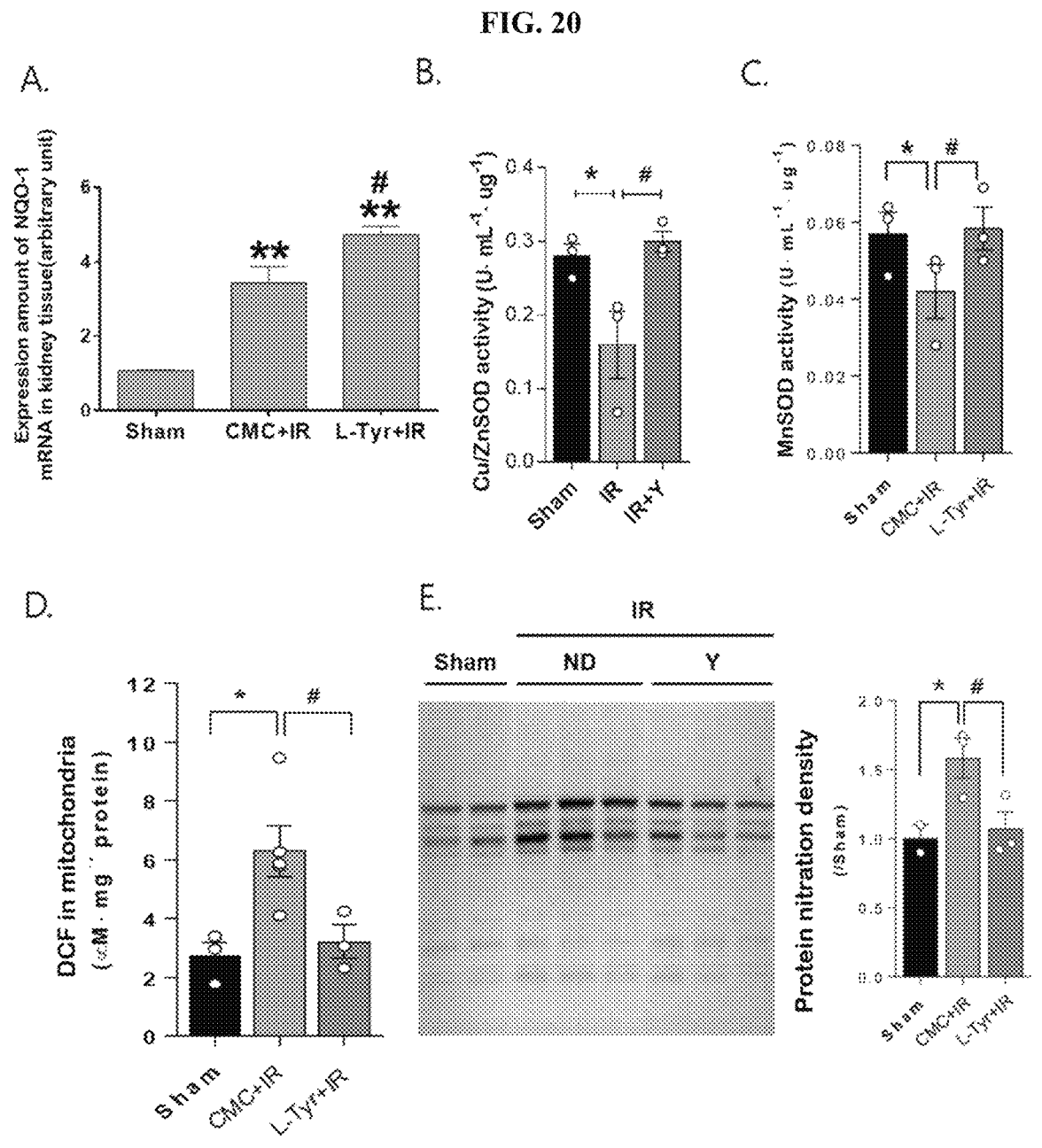

Oxidative stress caused by ROS (reactive oxygen species) or RNS (reactive nitrogen species) is involved in the main mechanism of acute renal failure, which is caused by kidney ischemia or reperfusion injury. In addition, increasing the anti-oxidation factors is important for suppressing kidney ischemia and reperfusion injury. Twenty-four hours after the kidney ischemia and reperfusion injury, expression of NQO-1 gene, which is an anti-oxidation factor, in kidney was measured. As a result, it was found that a statistically significant increase in the expression of NQO-1 gene is caused by the administration of L-tyrosine (#, $p<0.01$) compared to the group which has been administered with prepared solvent. ROS/RNS amount in mitochondria, which has been increased by 6 times or so due to IR, was also suppressed by Tyr. It was also found that lower activity of MnSOD and Cu/Zn SOD is caused by IR, but the activity was again recovered by Tyr. Twenty-four hours after the kidney ischemia and reperfusion, the amount of nitrotyrosine protein became higher in kidney tissues compared to the Sham group, but such higher amount was significantly reduced by the administration of L-tyrosine (FIG. 20).

Figure 21:
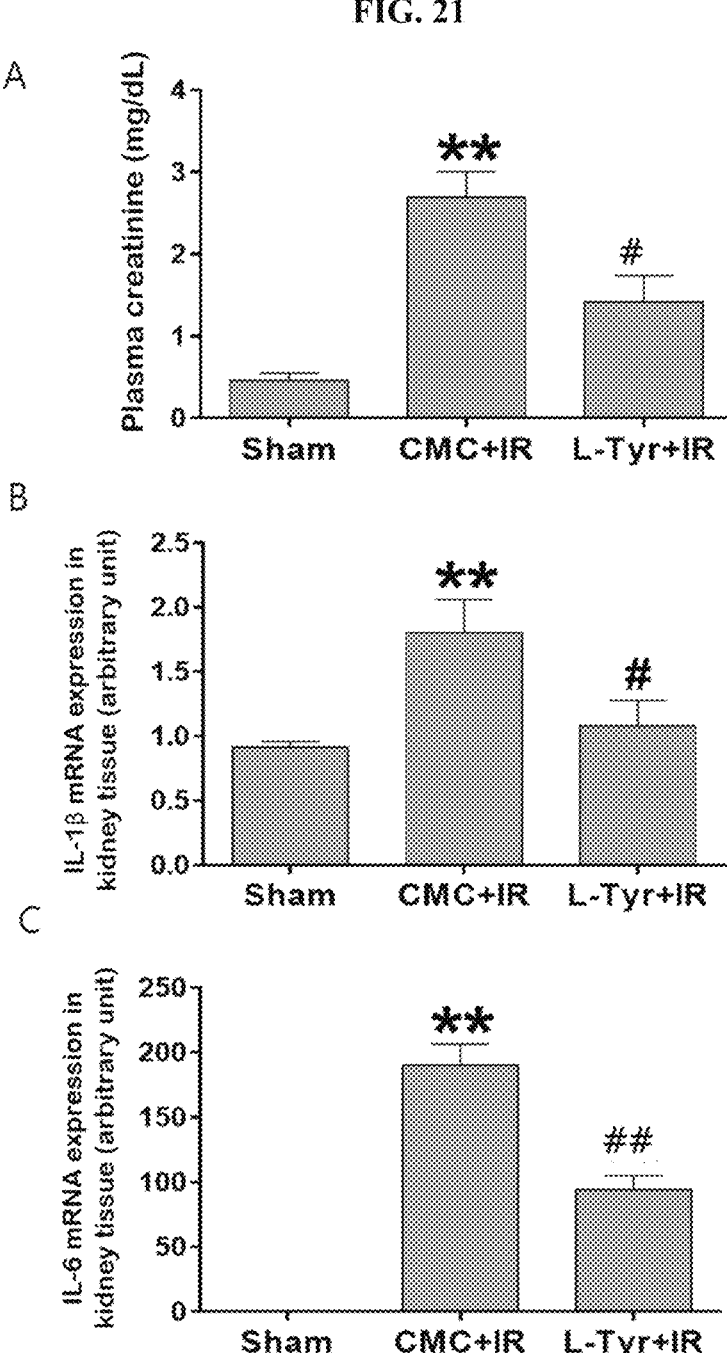
FIG. 21 shows the result of measuring plasma creatinine as an index for evaluating kidney injury. * and ** indicate that, compared to the Sham group, there is a statistically significant increase in expression amount of creatinine (A), IL-1β (B) and IL-6 (C), in which * has p<0.05 and ** has p<0.01. #and ##indicate that, compared to the CMC+IR group, there is a decrease in expression amount of creatinine, IL-1β, and IL-6, in which #has p<0.05 and ##has p<0.01.

Moreover, as a result of measuring creatinine in plasma as an index for evaluating kidney injury, it was found as illustrated in FIG. 21 that, 24 hours after kidney ischemia and reperfusion, the creatinine in plasma shows an increase of about 5.9 times compared to the Sham group, but such increase was suppressed again by the administration of L-tyrosine with statistical significance. To determine an inflammation response as a main mechanism of having acute renal failure based on kidney ischemia and reperfusion injury, gene expression of inflammatory cytokines (IL-1β and IL-6) in kidney tissues was examined. As a result, it was found that, 24 hours after kidney ischemia and reperfusion, the gene expression of IL-1β and IL-6 is higher than the Sham group, and such increase was suppressed by the administration of L-tyrosine with statistical significance.

Example 12. Test for Examining Effect of Tyr on Hepatic Encephalopathy (Hyperammonemia) Using Azoxymethane

(1) Animal Test

C57BL/6 male mouse (13-week old, KOATECH, South Korea) was allowed to have free access to diets and water in sterile breeding room with constant temperature and humidity. The animals were divided into 3 test groups, i.e., (1) Control group (Control), (2) Carboxymethyl cellulose+ azoxymethane treatment group (CMC+AOM), and (3) L-Tyrosine+AOM treatment group (L-Tyr+AOM). L-Tyrosine (100 mg/kg) was suspended in 0.5% CMC (carboxymethyl cellulose). The animal was orally administered, once a day for 4 days, with L-tyrosine or the prepared solvent CMC. Two hours after the oral administration on Day 4, intraperitoneal injection of AOM (100 mg/kg, 100 ml) was carried out. To prevent dehydration, the animal was intraperitoneally injected with 200 ml of physiological saline, 12 hours after the administration of AOM. Four hours after the injection, the test animal was sacrificed, blood was collected from the heart, and the liver tissues were harvested.

(2) Analysis of Ammonia in Blood

Amount of ammonia in blood was measured by using PocketChem BA PA-4140 (Arkray, Japan), which is an analytical device based on single wavelength reflectometry. Specifically, blood was applied in an amount of 20 μl on a test strip followed by reaction for 3 minutes. The strip was then inserted to the measurement device to obtain the absorbance at a wavelength of 635 nm (LED), which was then expressed in unit of μg/dl.

(3) Analysis of ALT in Plasma

Blood collected in the above was centrifuged for 15 minutes at 3,000 rpm to separate plasma, and ALT (alanine aminotransferase) as an index of liver cell injury was measured by using ChemiLab GPT Assay Kit (IVD-LAB, Korea). According to the standard measurement method of the kit, absorbance was measured at a wavelength of 340 nm, and then expressed in unit of U/L.

(4) Western Blot

Liver tissues were homogenized with RIPA buffer solution. After centrifuge for 15 minutes at 16,000×g, 4° C., supernatant was collected and the protein quantification was carried out by BCA method. After SDS-PAGE electrophoresis, proteins were transferred to a PVDF membrane, and then blocked with 5% skim milk. Following a reaction with nitro-tyrosine and β-actin primary antibody and corresponding secondary antibody, analysis was made with ChemiDoc XRS$^+$ System (Bio-Rad) according to ECL method.

Figure 22:
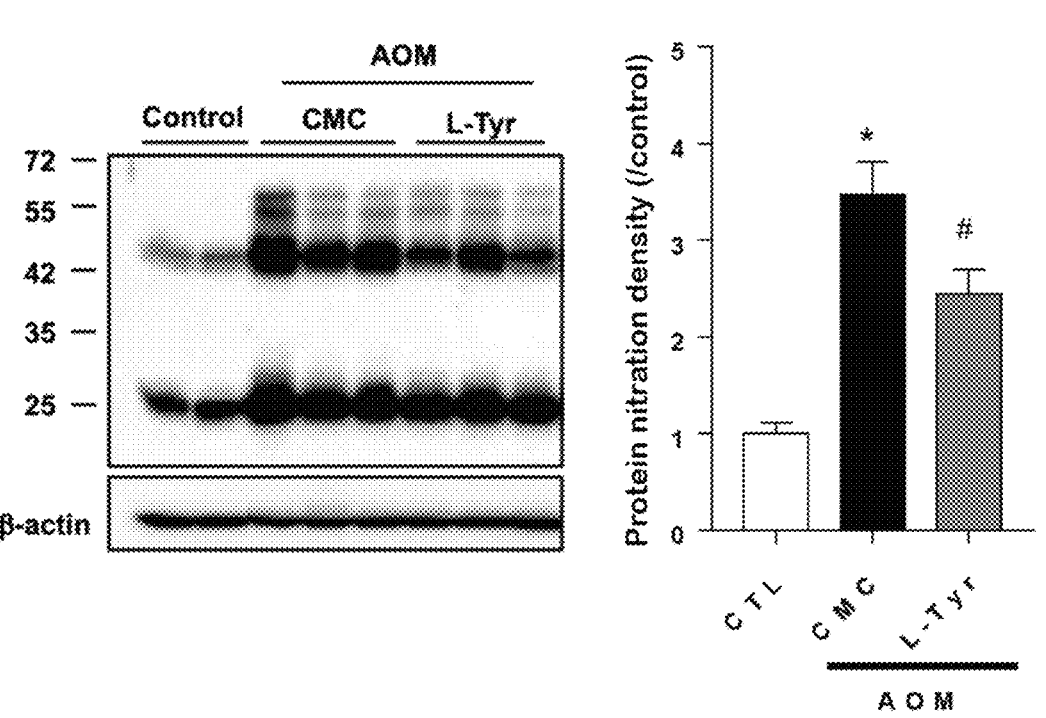
FIG. 22 shows the result of determining the effect of tyrosine on hepatic encephalopathy (hyperammonemia), in which (A) shows the ammonia content in blood, (B) shows ALT in plasma, and (C) shows the Western blot result of determining the amount of nitrated protein.

Ammonia is a main metabolite of amino acids and nucleic acids. Moreover, since key enzymes of the urea cycle for converting ammonia to urea are present only in liver cells, and GS and SOD, which can reduce the ammonia concentration, and catalase or the like that can remove active oxygen species are present in rich amount in liver tissues, a change in the blood ammonia concentration in blood vessel which is directed to brain via liver is a key indicator of hepatic encephalopathy. As a result of measuring blood ammonia in animal model of acute hepatic encephalopathy caused by AOM, it was found that the blood ammonia concentration of the CMC+AOM treatment group is about 6.7 times higher than the normal control group, but the increase in blood ammonia was suppressed by the administration of L-tyrosine with statistical significance. Since the injury of actual liver cells induces release of ALT in blood to yield higher ALT concentration in blood, measuring the activity of this enzyme can be a direct indicator which shows the severity of liver injury. Accordingly, ALT in plasma was measured in a model of acute hepatic encephalopathy caused by AOM. As a result, it was found that ALT in plasma of the CMC+AOM treatment group is about 65 times higher than the control group, but the increase in plasma ALT, which has been caused by AOM, was suppressed with statistical significance by the administration of L-tyrosine. In the liver tissues 16 hours after the administration of AOM, nitrotyrosine protein was found to be present in higher amount than the control group, but such increase was suppressed with statistical significance by the administration of L-tyrosine. These results can be the evidence supporting that nitration of the proteins present in liver is suppressed by Tyr so that the ammonia flown into the liver can be removed (FIG. 22).

Statistical Processing

All the data of the present invention are expressed in mean±SEM, and statistical analysis was made by using one-way analysis of variance (ANOVA) using Dunnetts Multiple Comparison Test or Student's t-test (p<0.05) using GraphPad Prism 5 (GraphPad Software).

Reference to an Electronic Sequence Listing

A sequence listing electronically submitted with the present application on Mar. 1, 2023 as an ASCII text file named 20230301_S05422GR10_TU_SEQ.TXT, created on Jan. 20, 2023 and having a size of 1,805 bytes, is incorporated herein by reference in its entirety.

---

What is claimed is:

1. A method for ameliorating or treating a disease caused by nitration of tyrosine in protein, the method comprising:

administering a composition comprising tyrosine or a salt thereof to a subject in need thereof, wherein the disease is selected from the group consisting of glaucoma, diabetes, diabetic retinopathy, cancer, acute kidney injury, hyperammonemia, and a combination thereof.

2. The method of claim 1, wherein the nitration of tyrosine in the protein is nitration of tyrosine in any protein selected from the group consisting of glutamine synthetase (GS), Mn superoxide dismutase, Cu/Zn superoxide dismutase, insulin receptor $\beta$ subunit, annexin IV, glutamate dehydrogenase, 3-$\alpha$-OH steroid dehydrogenase, glutathione S-transferase, 3-ketoacyl CoA thiolase, catalase, Tau protein, mitochondria complex 1, $\alpha$-synuclein, apolipoprotein-A1, amyloid-$\beta$, and NMDA receptor.

3. The method of claim 1, wherein the disease is a disease which occurs in liver, muscle, fat tissue, kidney tissue, pancreas, and/or lung.

4. The method of claim 1, wherein the composition is in a formulation selected from the group consisting of a pill, a tablet, a capsule, a powder preparation, powders, a granule, a candy, a syrup, and a drink.

5. The method of claim 1, wherein the composition is included in a functional health food.

6. The method of claim 1, wherein the composition is a pharmaceutical composition.

7. The method of claim 6, wherein the pharmaceutical composition further comprises at least one of a carrier, a vehicle, and a diluent.

* * * * *

SEQUENCE LISTING

```
<160> NUMBER OF SEQ ID NOS: 8

<210> SEQ ID NO 1
<211> LENGTH: 23
<212> TYPE: DNA
<213> ORGANISM: Artificial Sequence
<220> FEATURE:
<223> OTHER INFORMATION: IL-1beta f

<400> SEQUENCE: 1
tcgcagcagc acatcaacaa gag                                          23

<210> SEQ ID NO 2
<211> LENGTH: 23
<212> TYPE: DNA
<213> ORGANISM: Artificial Sequence
<220> FEATURE:
<223> OTHER INFORMATION: IL-1beta r

<400> SEQUENCE: 2
ggtgctcatg tcctcatcct gga                                          23

<210> SEQ ID NO 3
<211> LENGTH: 20
<212> TYPE: DNA
<213> ORGANISM: Artificial Sequence
<220> FEATURE:
<223> OTHER INFORMATION: IL-6f
```

<400> SEQUENCE: 3
ccaattcatc ttgaaatcac                                                             20

<210> SEQ ID NO 4
<211> LENGTH: 20
<212> TYPE: DNA
<213> ORGANISM: Artificial Sequence
<220> FEATURE:
<223> OTHER INFORMATION: IL-6r

<400> SEQUENCE: 4
ggaatgtcca caaactgata                                                            20

<210> SEQ ID NO 5
<211> LENGTH: 24
<212> TYPE: DNA
<213> ORGANISM: Artificial Sequence
<220> FEATURE:
<223> OTHER INFORMATION: NQO-1f

<400> SEQUENCE: 5
atgacatcac aggtgagctg aagg                                                       24

<210> SEQ ID NO 6
<211> LENGTH: 24
<212> TYPE: DNA
<213> ORGANISM: Artificial Sequence
<220> FEATURE:
<223> OTHER INFORMATION: NQO-1r

<400> SEQUENCE: 6
ctcaaaccag cctttcagaa tggc                                                       24

<210> SEQ ID NO 7
<211> LENGTH: 21
<212> TYPE: DNA
<213> ORGANISM: Artificial Sequence
<220> FEATURE:
<223> OTHER INFORMATION: GAPDHf

<400> SEQUENCE: 7
gtggcaaagt ggagattgtt g                                                          21

<210> SEQ ID NO 8
<211> LENGTH: 21
<212> TYPE: DNA
<213> ORGANISM: Artificial Sequence
<220> FEATURE:
<223> OTHER INFORMATION: GAPDHr

<400> SEQUENCE: 8
ttgactgtgc cgttgaattt g                                                          21